United States Patent
Yan et al.

(10) Patent No.: US 6,582,935 B2
(45) Date of Patent: Jun. 24, 2003

(54) ISOLATED NUCLEIC ACID MOLECULES ENCODING HUMAN ASPARTATE AMINOTRANSFERASE PROTEIN AND USES THEREOF

(75) Inventors: Chunhua Yan, Boyds, MD (US); Weiniu Gan, Gaithersburg, MD (US); Trevor Woodage, Washington, DC (US); Karen A Ketchum, Germantown, MD (US); Valentina Di Francesco, Rockville, MD (US); Ellen M Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/801,874

(22) Filed: Mar. 9, 2001

(65) Prior Publication Data

US 2002/0048801 A1 Apr. 25, 2002

Related U.S. Application Data

(60) Provisional application No. 60/207,350, filed on May 30, 2000.

(51) Int. Cl.[7] .............. C12P 21/00; C12N 1/21; C12N 15/85; C12N 15/63; C07H 21/04
(52) U.S. Cl. .............. 435/71.1; 435/252.3; 435/320.1; 435/325; 536/23.1
(58) Field of Search .............. 435/71.1, 320.1, 435/325, 252.3; 536/23.1

(56) References Cited

FOREIGN PATENT DOCUMENTS

| | | | |
|---|---|---|---|
| EP | 1033401 A | 9/2000 | |
| WO | WO 01/57270 A | 8/2001 | |

OTHER PUBLICATIONS

Database EMBL Online!: Oct. 16, 1998, Strausberg, R. "qf57/co2.xl Soares testis NHT Homo sapiens cDNA clone Image: 17541143" similar to SW:AATC Chick P00504 Aspartate Aminotransferase, Cytoplasmic; contains Alu repetititve element;, mRNA sequence Database Accession No. A1204203.

Database EMBL Online!: Sep. 28, 1999; Hirakawa, M. et al. "Homo sapiens genomic DNA, chromosome 8p11, clone:9lj23 to 9–41." Database Accession No. AP000501.

Database EMBL Online!: Feb. 8, 2001: Adachi, J. et al.: "Mus musculus adult male testis cDNA, Riken full–length enriched library, clone: 1700083M11: homolog to Aspartate Aminotransferase, Cytoplasmic (EC 2.6.1.1) (Transaminase A) (Glutamate Oxaloacetate Transaminase–1), full insert sequence." Database accession No. AK006984.

*Primary Examiner*—W. Gary Jones
*Assistant Examiner*—Jehanne Souaya
(74) *Attorney, Agent, or Firm*—Celera Genomics; Justin Karjala

(57) ABSTRACT

The present invention provides amino acid sequences of peptides that are encoded by genes within the human genome, the aminotransferase peptides of the present invention. The present invention specifically provides isolated peptide and nucleic acid molecules, methods of identifying orthologs and paralogs of the aminotransferase peptides, and methods of identifying modulators of the aminotransferase peptides.

17 Claims, 11 Drawing Sheets

```
   1 CTTGGAGGAA GACTTCTGGG CAGAAGCGGA ACACAGGAGC AGAGACACAT
  51 AGTCTTGGCT CCAGTTTCGT TTCAGTTATG CCCACCCTTT CAGTGTTCAT
 101 GGATGTGCCC CTCGCCCACA AGCTAGAGGG CAGCTTGTTA AAGACCTACA
 151 AACAAGATGA TTACCCGAAC AAGATATTCT TAGCCTATAG AGTCTGCATG
 201 ACAAATGAAG GCCATCCCTG GGTTTCTCTC GTGGTGCAGA AGACTCGACT
 251 ACAGATTTCA CAGGATCCCT CCCTGAATTA TGAGTACTTG CCCACCATGG
 301 GCCTGAAATC ATTCATCCAG GCCTCTCTAG CACTCCTCTT TGGAAAGCAC
 351 AGCCAAGCCA TTGTGGAGAA CAGGGTAGGG GGTGTACACA CTGTTGGTGA
 401 CAGTGGTGCC TTCCAGCTTG GCGTCCAGTT TCTCAGAGCT TGGCATAAGG
 451 ATGCTCGTAT AGTTTACATC ATCTCTTCTC AAAAAGAACT GCATGGACTC
 501 GTCTTCCAGG ACATGGGCTT TACAGTTTAT GAATACTCTG TCTGGGACCC
 551 CAAGAAGCTA TGCATGGACC CCGACATACT CCTCAATGTG GTGGAGCAGA
 601 TCCCACATGG CTGTGTCCTT GTGATGGGGA ACATTATCGA CTGCAAGTTG
 651 ACACCAAGTG GGTGGGCAAA GTTGATGTCC ATGATAAAGA GCAAGCAGAT
 701 ATTCCCATTT TTTGATATTC CCTGTCAAGG TTTATACACC AGTGACTTGG
 751 AAGAAGATAC TAGAATCTTA CAATACTTTG TGTCTCAAGG CTTTGAGTTC
 801 TTCTGCAGCC AGTCTCTGTC CAAGAATTTT GGCATTTATG ATGAAGGAGT
 851 GGGGATGCTA GTGGTGGTGG CAGTCAACAA CCAGCAGCTG CTGTGTGTCC
 901 TCTCCCAGCT GGAAGGATTA GCCCAGGCCC TGTGGCTAAA CCCCCCCAAC
 951 ACGGGTGCAC GTGTCATCAC CTCCATCCTC TGCAACCCTG CTCTGCTGGG
1001 AGAATGGAAG CAGAGTCTAA AAGAAGTTGT AGAGAACATC ATGCTAACCA
1051 AGGAAAAAGT GAAGGAGAAA CTCCAGCTCC TGGGAACCCC TGGGTCCTGG
1101 GGTCACATCA CCGAGCAGAG TGGGACCCAC GGCTATCTTG GACTCAACTG
1151 TAAGGGTCTA GGGGGCTGGT GTCCCCCCTT TCTGACCTTT GGCCTGTATT
1201 TGAGCATTAA ACTTCACTGA CTAGGTGACC AGTTCCTAGC TTCACTCCAG
1251 ATTTTGATTC TGTCCTCTGG AAAATGGGCT GCTTTAAAGA CACTTCTGGA
1301 CCCCCAGAAG TACCGACACT CCCTATCCTT CATAAACCAG CCTGGGTGCC
1351 CGGTGCAGTG GCTCATGCCT GTAATCCCAA CACTTTGAGA GGCCGAGGCG
1401 GGTGGGTCAC CTGAGGTCAG GAGTTCGAGA CCAGCCTGGC CAACATGGTG
1451 AAACCCCGTC TCTACTAAAA AATAAAATAT GAAAATTAAA AAAAAAAAA
1501 AAAAAAAAAA AAAAAAA   (SEQ ID NO:1)
```

FEATURES:
5'UTR:       1-77
Start Codon: 78
Stop Codon:  1218
3'UTR:       1221

FIGURE 1A

HOMOLOGOUS PROTEINS:
Top 10 BLAST Hits:

```
                                                                    Score      E
CRA|98000043614490 /altid=gi|12840318 /def=dbj|BAB24820.1| (AKO...    394    e-108
CRA|18000004996940 /altid=gi|105387   /def=pir||S13035 aspartate ...  271    2e-71
CRA|18000004889577 /altid=gi|4504067  /def=ref|NP_002070.1| aspa...   271    2e-71
CRA|18000004933294 /altid=gi|6754034  /def=ref|NP_034454.1| glut...   268    2e-70
CRA|18000004990989 /altid=gi|90313    /def=pir||S01076 aspartate t... 266    6e-70
CRA|18000004889578 /altid=gi|345752   /def=pir||S29028 aspartate ...  266    6e-70
CRA|18000004930537 /altid=gi|91997    /def=pir||JT0439 aspartate t... 265    1e-69
CRA|18000004988459 /altid=gi|809192   /def=pdb|2CST|A Chain A, As...  263    5e-69
CRA|18000004942671 /altid=gi|112971   /def=sp|P00504|AATC_CHICK A...  263    5e-69
CRA|18000004886125 /altid=gi|229661   /def=pdb|1AAT|     Cytosolic... 262    7e-69
```

BLAST dbEST hits:

```
                                           Score      E
gi|3756809  /dataset=dbest /taxon=9606 ...   882    0.0
gi|2806066  /dataset=dbest /taxon=9606 ...   839    0.0
gi|12346937 /dataset=dbest /taxon=96...      587    e-165
gi|2884996  /dataset=dbest /taxon=9606 ...   424    e-116
```

EXPRESSION INFORMATION FOR MODULATORY USE:
library source (from BLAST dbEST hits):
gi|3756809  testis
gi|2806066  testis
gi|12346937 Testis
gi|2884996  testis Tissue expression:
Human testis

FIGURE 1B

```
  1 MPTLSVFMDV PLAHKLEGSL LKTYKQDDYP NKIFLAYRVC MTNEGHPWVS
 51 LVVQKTRLQI SQDPSLNYEY LPTMGLKSFI QASLALLFGK HSQAIVENRV
101 GGVHTVGDSG AFQLGVQFLR AWHKDARIVY IISSQKELHG LVFQDMGFTV
151 YEYSVWDPKK LCMDPDILLN VVEQIPHGCV LVMGNIIDCK LTPSGWAKLM
201 SMIKSKQIFP FFDIPCQGLY TSDLEEDTRI LQYFVSQGFE FFCSQSLSKN
251 FGIYDEGVGM LVVVAVNNQQ LLCVLSQLEG LAQALWLNPP NTGARVITSI
301 LCNPALLGEW KQSLKEVVEN IMLTKEKVKE KLQLLGTPGS WGHITEQSGT
351 HGYLGLNCKG LGGWCPPFLT FGLYLSIKLH    (SEQ ID NO:2)
```

FEATURES:

Functional domains and key regions:
[1] PDOC00005 PS00005 PKC_PHOSPHO_SITE
Protein kinase C phosphorylation site Number of matches: 4
```
      1     23-25   TYK
      2    134-136  SQK
      3    313-315  SLK
      4    376-378  SIK
```

[2] PDOC00006 PS00006 CK2_PHOSPHO_SITE
Casein kinase II phosphorylation site

Number of matches: 7
```
      1    105-108  TVGD
      2    134-137  SQKE
      3    149-152  TVYE
      4    154-157  SVWD
      5    222-225  SDLE
      6    276-279  SQLE
      7    313-316  SLKE
```

[3] PDOC00008 PS00008 MYRISTYL
N-myristoylation site

Number of matches: 5
```
      1    101-106  GGVHTV
      2    218-223  GLYTSD
      3    280-285  GLAQAL
      4    336-341  GTPGSW
      5    372-377  GLYLSI
```

Membrane spanning structure and domains:

| Helix | Begin | End | Score | Certainity |
|---|---|---|---|---|
| 1 | 70 | 90 | 0.893 | Putative |
| 2 | 257 | 277 | 0.641 | Putative |
| 3 | 359 | 379 | 1.393 | Certain |

BLAST Alignment to Top Hit:
```
>CRA|98000043614490 /altid=gi|12840318 /def=dbj|BAB24820.1|
       (AK006984) putative [Mus musculus] /org=Mus musculus
       /taxon=10090 /dataset=nraa /length=264
       Length = 264

Score =  394 bits (1001), Expect = e-108
 Identities = 185/254 (72%), Positives = 213/254 (83%)
 Frame = +3

Query: 78   MPTLSVFMDVPLAHKLEGSLLKTYKQDDYPNKIFLAYRVCMTNEGHPWVSLVVQKTRLQI 257
            M +LSVF DVP A KLEGSLLK Y+QD YP+K+FLAY+VCMT EGHPWVSLVV KTRLQI
Sbjct: 1    MTSLSVFRDVPTAQKLEGSLLKIYRQDGYPSKLFLAYKVCMTEEGHPWVSLVVHKTRLQI 60
```

FIGURE 2A

```
Query:: 258 SQDPSLNYEYLPTMGLKSFIQASLALLFGKHSQAIVENRVGGVHTVGDSGAFQLGVQFLR 437
            ++DPSL+YEYLP +GLKSFIQ+SL LLFGKHS+AI E RVGGVH VG+SGAFQLG QFL+
Sbjct:  61 AEDPSLDYEYLPLVGLKSFIQSSLELLFGKHSEAIAEKRVGGVHIVGESGAFQLGAQFLK 120

Query: 438 AWHKDARIVYIISSQKELHGLVFQDMGFTVYEYSVWDPKKLCMDPDILLNVVEQIPHGCV 617
            W K+ +IV I+S QKE  GL+FQDMGF VYEYS+W+   LC DP + + V++ IP G +
Sbjct: 121 TWRKNVKICVISCQKEQCGLIFQDMGFIVYEYSIWNASDLCSDPSMFVEVLQHIPVGSI 180

Query: 618 LVMGNIIDCKLTPSGWAKLMSMIKSKQIFPFFDIPCQGLYTSDLEEDTRILQYFVSQGFE 797
            LV+GNI DCK T + W KLMS+IKSKQIFPFFDIPCQGL T DLEEDT+ILQYFVS G E
Sbjct: 181 LVIGNITDCKFTQNQWTKLMSIIKSKQIFPFFDIPCQGLSTGDLEEDTKILQYFVSLGLE 240

Query: 798 FFCSQSLSKNFGIY 839
            FFCSQSLSKNFGIY
Sbjct: 241 FFCSQSLSKNFGIY 254    (SEQ ID NO:4)

>CRA|18000004996940 /altid=gi|105387 /def=pir||S13035 aspartate
        transaminase (EC 2.6.1.1) - human /org=human /taxon=9606
        /dataset=nraa /length=412
        Length = 412

Score =  271 bits (685), Expect = 2e-71
  Identities = 145/365 (39%), Positives = 208/365 (56%), Gaps = 10/365 (2%)
  Frame = +3

Query:  90 SVFMDVPLAHK-LEGSLLKTYKQDDYPNKIFLAYRVCMTNEGHPWVSLVVQKTRLQISQD 266
           SVF +VP A    L     L    ++D P K+ L      T++  HPWV  VV+K   +I+ D
Sbjct:   4 SVFAEVPQAQPVLVFKLTADFREDPDPRKVNLGVGAYRTDDCHPWVLPVVKKVEQKIAND 63

Query: 267 PSLNYEYLPTMGLKSFIQASLALLFGKHSQAIVENRVGGVHTVGDSGAFQLGVQFLRAWH 446
           SLN+EYLP +GL  F    +    L G  S A+  E RVGGV ++G  +GA ++G  FL  W+
Sbjct:  64 NSLNHEYLPILGLAEFRSCASRLALGDDSPALKEKRVGGVQSLGGTGALRIGADFLARWY 123

Query: 447 KDARI----VYIISSQKELHGLVFQDMGFT-VYEYSVWDPKKLCMDPDILLNVVEQIPHG 611
                    VY+ S   E H  VF  GF + Y WD +K  +D    LN +E  P
Sbjct: 124 NGTNNKNTPVYVSSPTWENHNAVFSAAGFKDIRSYRYWDAEKRGLDLQGFLNDLENAPEF 183

Query: 612 CVLVMG----NIIDCKLTPSGWAKLMSMIKSKQIFPFFDIPCQGLYTSDLEEDTRILQYF 779
            ++V+     N      TP W ++ S++K + +FPFFD  QG + + +LE D   ++YF
Sbjct: 184 SIVVLHACAHNPTGIDPTPEQWKQIASVMKRRFLFPFFDSAYQGFASGNLERDAWAIRYF 243

Query: 780 VSQGFEFFCSQSLSKNFGIYDEGVGMLVVVAVNNQQLLCVLSQLEGLAQALWLNPPNTGA 959
           VS+GFEFFC+QS SKNFG+Y+E VG L VV      + +L VLSQ+E + +   W NPP  GA
Sbjct: 244 VSEGFEFFCAQSFSKNFGLYNERVGNLTVVGKEPESILQVLSQMEKIVRITWSNPPAQGA 303

Query: 960 RVITSILCNPALLGEWKQSLKEVVENIMLTKEKVKEKLQLLGTPGSWGHITEQSGTHGYL 1139
           R++  S L NP L  EW ++K + + I+   + +++ +L+  L TPG+W HIT+Q G   +
Sbjct: 304 RIVASTLSNPELFEEWTGNVKTMADRILTMRSELRARLEALKTPGTWNHITDQIGMFSFT 363

Query: 1140 GLNCK 1154
            GLN K
Sbjct: 364 GLNPK 368    (SEQ ID NO:5)

Hmmer search results (Pfam):
Model       Description                                    Score      E-value   N
PF00155     Aminotransferases class-I                       85.6       1.1e-24   2

Parsed for domains:
```

FIGURE 2B

| Model | Domain | seq-f | seq-t | hmm-f | hmm-t | score | E-value |
|---|---|---|---|---|---|---|---|
| PF00155 | 1/2 | 44 | 131 .. | 47 | 142 .. | 22.6 | 5.8e-06 |
| PF00155 | 2/2 | 191 | 349 .. | 212 | 393 .. | 62.9 | 5.9e-18 |

FIGURE 2C

```
   1 CCAGTATGGT CTCAATCTCC TGTCCTTGTG ATCTGCCTGT CTTGGCCTTC
  51 CAAAGTGCTG GGATTACAGG TGTGAGCCAC CGTGCCCGAC CTTTTTTTTT
 101 TTTTAAAGAC AGGATCTCAC TCTGTCAACC AGGCTGGAGT GCAGTGCCAT
 151 GATCATAGCT CACTGCAATA CCACCACGCC CAGCTAATTT TAAAATTTTT
 201 TGTGGAGTGG GTGGGGGGGG TCTCCCTATG TTGCTCAGGC TGGTCTTGAG
 251 CTCCTGGGCT CAAGTGATCC TCCCGCCTCA GTCTCCCAAA GCACTAGGAT
 301 TGCAGGTGTG AGCCACCATG CCTGGCTGTG GCTGACCCTT TGTATGCCTA
 351 AATCAGGCAG TCATTGGCTA CCCCTGTCAG TGGGGGTGAA ACCTCCAGGT
 401 GGTTTCTAGG CTAGCTGACT CCTGCCAGCC AAGCACAATT CTCCAGAGAA
 451 CACAGGCATA TAAGCCTTGT CCACCAGCGA AGCAGCAGCT GGGGCCGGGC
 501 ACATTGGTGG TGAAGGCCTT CTGGGTGAGA CATCAACAGT GTTTGCAACA
 551 ATCATTTAAA GAGTTATTTA ACATCAGGCT GGGTGTGGTG GCTCATGCCT
 601 GTAATCCTAA CACTTTGGGA GGCTGAGGTA GGCAGATCAC TTGAGGTCAG
 651 GAGTTTGAGA CCAGTCTGGC AACGTGGTG AAACCCTGTC TCTACTAAAA
 701 ATACAAAAAA AAGCCGGGCG CAGTGACTCA CGCCTGTAAT CCCAGCACTT
 751 TGGGAGGCCC AGGTGGGCAG ATCACCTGAG GTCTGGAGTT TGAGACCAGC
 801 CTGATCAACA TGGAGAAATC CCCCTCTCTA CTAAAAATAC AAAATTAGTT
 851 GGGTGTGGTG GCGCATGCCT GTAATCCCAG CTACTCGGGA GGCTGAGGCA
 901 GGAGAATCTC TTGAACCTGG GAAGCAGAGG TTGCAGTGAG CCGAGATCAC
 951 ACCACTGCAC TCCCAAGTGG GCAGCAAGAG CGAGACTCTG TCTCAAAAAA
1001 AAAAGAGAGA GTCATTAAAC ATCAAAAGGA AAGAAAGCA AGCAATATGC
1051 AGACTGACTC TATAGAGGCT GGCTCTTTC TCCCCTTGGC CTCTGCTGTC
1101 TATACTTACT AGTTGGCTGT CATTGAAACT TAACAAATGG CCAGGTGTGG
1151 TGGCTCATGC CTGTAATCCC AGCAGTTTGG GAGGCCAAGG CAGGCAGATC
1201 ACCTGAGGCA AGGAGTTCGA GACTATCGAC AAAGTGAGAC TCCATCTCAA
1251 AAAAAAAAAA AACCAAAAAA AGAAAGAAAA AGAAACTTAA CAAACATATG
1301 TAGAAGTCTT GGCTCTAGAT AACTGAGAGA AATAGGACTG GCTTAGTGAG
1351 TTGCCAATTA TATTCTAATA ATAGGATTCT TTATTAAAAC AACTGTGGAA
1401 GAAAACAGTG TTTGCTTTTT ATTCCTTTTG AAATCTGGGG CACTTTGCAA
1451 AATGGAAATC AATGCCTCGA CTTGCATTGG TGTGTGATCT GGGGTTTTTG
1501 CTTCTGCAGG AGAAGCCCTA TCTGGCTTAT TGGCTGCCTG CCTTGCCCTA
1551 TGTCTTTCTT TCTTTTTTTT TTTTTAATT TGTATAAATG TGTGAAGTAC
1601 AAGTGTAATT TTGTTAGATG CATACATCGC ATAGTGGTGA AGTCAGGGCT
1651 TTTAGGGTAT CCATAACCCC AACAATGTAC ATTGTATCTG TTAAGTAATC
1701 TCCCATTATC CTTGCCCTGT CATCTAAGGA GTGGGCTTGT TACTTTGGAC
1751 TGAGCCACCT GGGGCTAGAG AAGAGAAGGC ATTGAGTGAG GGAAACGGGC
1801 TTGGGAATTC CGGAGATTGT TATCCTGCCC TGCCCGCTGT CTGAGGGGAT
1851 TCTCCTCAAG TACCCTGGAA TGTTCCTGTG GCCCTGTGG ATCGCCACCA
1901 CAAAGATCAT GAGGTTCTGT TGCCCTGGCA ACCCGTTGTC CAGCGCCTCT
1951 GCACTGGGGC TGCCAAGGTT CCAGGAAGAG GCAGGACTGC CCGGCCCAGC
2001 CTTGGAGGAA GACTTCTGGG CAGAAGCGGA ACACAGGAGC AGAGACACAT
2051 AGTCTTGGCT CCAGTTTCGT TTCAGTTATG CCCACCCTTT CAGTGTTCAT
2101 GGATGTGCCC CTCGCCCACA AGCTAGAGGG CAGCTTGTTA AAGACCTACA
2151 AACAAGATGA TTACCCGAAC AAGATATTCT TAGCCTATAG AGGTAGATGC
2201 CTAGCAGTTC TGAAGTATAA GACTTAAGTG ATGGTAACTG CCTCTAGGAG
2251 GACAGTGTTC CCTGCTGCAG GGGGAGGGGT GCAGCCCAAG CTTCTGTGGG
2301 TGGAGAGATC TTTTCTTGTT AACAGAATTA CCCAGTGGGG AAAAGTGCAG
2351 ATAAGGTCCC AGGTCATTCC ATGCTCTCTG CCCTTCTCTG GGGGCTTCTA
2401 GGGATTTGGT GAGAGCTATG TCCTCTTCCA CAACTCTATG CTTGGGGGCC
2451 TGCATGGCCA TCCCACACTT CTTCAGATTC TTACCTCCTC TCTCTCTCTT
2501 TCTCTTTCTC TTCCTGTTCT TGAACCAAGA ATGGTTCTCC AGATTGAGCC
2551 TTCTGCTATG CAACTGGGGC TCACCACTGT GAAAGTCAGG GTTACCTTTA
2601 TTTAGCTTCA TCTACCTATA ACTCTCATTT GCATATATA TATATATATA
2651 TATATATATA TATATATATA TATATATA TTTTTTTTTT TTTTCTTGAG
2701 ACAGGGCCTC ACTCTGTTGC CCAGGCTGAA GTGCAGTGGC AAGGATCTCA
2751 GCTCACTGCC ACCTTTGCCT CCTGGGCTCA ACCATCCTC TTGCCTCAGC
2801 CTCCTGAGTA GCTGGGACTA CAGGCGCTGG TCACCATGTC TGGCTGTTTT
2851 GTATTTTTTT GTAGAGACAG GGTTTCATCA TGTTGCCCAG GCTGATCTTG
2901 AACTCCTGAA CTCAAGTGAT CCACCCACCT TAGCCTCCCG AAGTGCTGGG
2951 ATTACAGGCC TGAGCCACCA ATCCTGGGCT TGTATGATTT TTAACCTTTA
3001 AAATGGCATA GGTTTCAGTT GTCTTTTTTA AAAAGACAAA AATAATACAC
3051 ATTCACTAAC AGCATATTCT TTTCATCAAG GAGAAAAGAA AAGGGAAAGT
```

FIGURE 3A

```
3101 TGTATTTTCA CAGGCACCTT CCCACAGCCC CATGGAGTCC AGGAGAGATT
3151 TGTTTGCAGG CTGTCTGCAG AGCTCAGCCC TGGGGGCCCA AACCAGGCAT
3201 CTGGAGCTCC CTCTGTGGTT TTCCTCACAG TCTGCATGAC AAATGAAGGC
3251 CATCCCTGGG TTTCTCTCGT GGTGCAGAAG ACTCGACTAC AGATTTCACA
3301 GGATCCCTCC CTGAATTATG AGTACTTGCC CACCATGGGC CTGAAATCAT
3351 TCATCCAGGC CTCTCTAGCA CTCCTCTTTG GAAAGCACAG CCAAGCCATT
3401 GTGGAGAACA GGGTGAGAAG GTGGGCCCTC CCCTGGCTCA TTTAGACACA
3451 GAGAGTGGCG ATCTGGGTCT GCACAACCTT AAACCCGAAG GGGACCTCGG
3501 AGGGCCCCCT GGTATTGATA AAAGAGATAC CTGAGGCTCA GAGAGTCCAC
3551 AAGTCCTTAG CCATCGAGTC AGGATCGGAA TCTCAGTCCA GTGGTATTCC
3601 CACCTGCTCA CACTGCTGAT TTGAAAGCTC TTTCAAGACA GGAATGATCT
3651 GAATTGGAGG TGGTGTTAGT ATTCCCATTA CTGTTTTATT TTTTAACCTA
3701 TTATATATAT TTTTTGAGAC AGAGTCTCAC TCTGTCACCC AGGCTAGAGT
3751 GCAGTGGTGC CATCTCAGCT CACTGCAACC TCCACCTCCC AGGTTCAAGC
3801 AATTCTGGTG CTGCATCCTC CTGAGTAGCT GGAATACAG GCATGTGCCA
3851 TCACGCCCAG CTAATTTTTG TATTTTTTGT AGAGACAGGG TTTCACCATG
3901 TTGGCCAGGC TGGTCTCAAA CTCCTGGCCT CAGGGGATTC CCTGCCTCGT
3951 CCTCCCAAAG TGCTGGGATT ACAGGCATGA GCTACTGCGT CTCGCCTCCA
4001 TTACTGTTTT AGAGTGTTAT TTCTGTCTAT TTCTTTTTAT TTTTAATGT
4051 TTATTTACTT ATTATTTTTT TGAGACGGAG TCTCACTCTG TCACCCAGAC
4101 TGGAGTGCAG TGGCCTGATC TCCGCTCACT GCAACTTCCG CCTTCCGGGT
4151 TCAAGTGATT CTCCTGCCTC AGCCTCTTGA GTAGCGGGGA TTACAGGTGC
4201 CCAACACCAC ATCCGGCTAA TTTTTGTATT TTTAGTAGAT ACGGGGTTTC
4251 AACATGTTGG CCATGACCTC GAGTGATCCA CCCACCCCGG CCTCCCAAAG
4301 TGCTGGAATT ACAGGTGTGA GCCACCACAC CTGGCCTATT TGTGTCTATG
4351 TCTTGCTGGC AGGTAGGGGG TGTACACACT GTTGGTGACA GTGGTGCCTT
4401 CCAGCTTGGC GTCCAGTTTC TCAGAGCTTG GCATAAGGAT GCTCGTATAG
4451 TTTACATCAT CTCTTCTCAA AAAGGTTAGT CTTACCCAAG ATGAGGGGAA
4501 CAGCAATCCC CGTCCCTTGT TCCTAATCCT CACCCCATTT GCCATCTTCA
4551 CTGTTATCCC TCATTCTCTG TCATGAGCAA AATGGCAGAC AAGCCAAGCT
4601 ATTTATGTCC TTTTCCTGTT AATGTCCCAC CTTCAGCCAG TGACTCTCAG
4651 CCCCACACTC CAGTACCTCT GTCTCCGTCT CTCTGTTTCC CATGTACCAG
4701 CTAGTGGGGG GCTGTGTTCC CACAGAACTG CATGGACTCG TCTTCCAGGA
4751 CATGGGCTTT ACAGTTTATG AATACTCTGT CTGGGACCCC AAGAAGCTAT
4801 GCATGGACCC CGACATACTC CTCAATGTGG TGGAGGTAGA GGGGCCCCGC
4851 TCAGAAACTC CTCCCTAGAG CTGACTTACA GCCTAATGTT CCTCTCCTCC
4901 CCACACCTCT TAAGTCATCC AAGACCTTTT CCAGGTTTGA ATTTGCCTGG
4951 CCCTTCAATG GTAACTAACA TGGAGGAGCA CTTCACCCCC AAATGCCCTG
5001 GGGCCGCCAC TCCTGGGTGG GGGTGAAGCC TGATGAGACC GTCTGTACCT
5051 GCAGCAGATC CCACATGGCT GTGTCCTTGT GATGGGGAAC ATTATCGACT
5101 GCAAGTTGAC ACCAAGTGGG TGGGCAAAGT TGATGTCCAT GATAAAGGTA
5151 AACCCAATCT CCCACCCGAC CTTCCTGTCT TTGACTCTCT GCTCTCTCCT
5201 CCATCTGTCT CATTCTTTTT TTGTTCTCCT TTCTCCTACA GAGCAAGCAG
5251 ATATTCCCAT TTTTTGATAT TCCCTGTCAA GGTTTATACA CCAGTGACTT
5301 GGAAGAAGAT ACTAGAATCT TACAATACTT TGTGTCTCAA GGCTTTGAGT
5351 TCTTCTGCAG CCAGTCTCTG TCCAAGAATT TTGGCATTTA TGGTATGGTA
5401 CAGGCAGAAG AAGGGAGGGT CTGTTGCTGA AGTGGCTGTG CGCTCACAGC
5451 ACAGTGATGT TTTTGATATC TCATCCTTGG GAGGGAGCCA AGGACTCTAG
5501 GGAGAGCACT ATAGAAGCAG AAGTGGGGAG CACTGAGCTA GAATTTGGTT
5551 CTGTTACTAA ATCTAGTAAC AGAACCCAAC CCAGCTTGGC TTGGATCATT
5601 TCACCCCCTC AGGCCTCTGT TTCCTCAACT ATAAGATGAG AGGGTGGGGC
5651 TGGCATGGTG GGTGACACCT GTAATCCCAG TTGACACCTC CTAATCCCTC
5701 CTTTGGGAGG TCAAGGTTAG GTGATCACTT GAGGCCAGGA ATTCAAGACC
5751 AGCCTGGGCA ACACACCGAG ACCCGGTCTC TACAAACAAT TAAAAAAATT
5801 AGTCGGGCAT GGTGGTACAC ACCAGTAGTC CTACCCACCC GGGGGGCTGA
5851 GGCAGGAGGA TTGCTTAAGC CCAGGAGGTA GAGGTTGCAG TGAGCTATGA
5901 TTCCACCATT GCACTCTAGC CTGGGCAACA GAGAGAGATG GTCACTTTAA
5951 ACAAATAAAA ATAAAAATAA AAATAATAAA GGAAAGGAAA GGAAAAAACA
6001 GGAGAGTAGA ACTTAGTGAT CTTTCAAATT CCTTCCTCCT TTAAGACTCT
6051 GACTTATGGG TACTTTTGCT GGAAGGAGAG CCTCTGGCAA CTTCCCGGAG
6101 CCTGAATATC ACCCTGGCTG GGCTGCAATG AGGGCCTTGT GGTTCAACCC
6151 TTTCTTCTGC AAGGTTGGGG GTTGAGATCT AGGTGAAGGC CTTGGGAGTG
```

FIGURE 3B

```
6201 GAGGAAGGGG CTGAGGCTGA GGCTGTCTTC CCAACACTGC AGATGAAGGA
6251 GTGGGGATGC TAGTGGTGGT GGCAGTCAAC AACCAGCAGC TGCTGTGTGT
6301 CCTCTCCCAG CTGGAAGGAT TAGCCCAGGC CCTGTGGCTA AACCCCCCCA
6351 ACACGGGTGC ACGTGTCATC ACCTCCATCC TCTGCAACCC TGCTCTGCTG
6401 GGAGAATGGT AAGGGTGAGG GCTGGAGCAG GAAGGGATGG GAGAGGCCCT
6451 GGGTGCCTGC AGACCTGCTG ATCTGCAGGA TTCGGCAGGG TGCTTCTCTC
6501 CTGCCCATGT GGCCTTTTTA CTCCATTCAT TCATCAACAT TTACTAAGGA
6551 CCTGATGTGT ACCAATGGCG GTGGCTATGC CAAGGGTTGC CTTAGGGGAC
6601 AGAGTGATAG GACATTTGTT TTGCACCCAG GCCAATGAGT TATATGAACT
6651 CTTCCAGATT GCTTGGGGAG ATAAGAGAGC ATCAGGGGCT TGCAACTCTG
6701 GCAAAATCTG CCTGGGAGCC TCCCTGGTTT GCTTAAATGA ATATGAGATC
6751 AAACCTCCCT CCCACTCATA ATCATCCCAG AGCCTCTGGC ACTCTGTTGG
6801 AGACCTTTGA AGGTAAGAAG AGTGGACTGG CAATGAGGGA GGTTTGAGGG
6851 CAAGGGGGAC CTCACACCCT CCTTTCTCAT TGTCCTTCCT TGGTAGGAAG
6901 CAGAGTCTAA AAGAAGTTGT AGAACACATC ATGCTAACCA AGGAAAAAGT
6951 GAAGGAGAAA CTCCAGCTCC TGGGAACCCC TGGGTCCTGG GGTCACATCA
7001 CCGAGCAGAG TGGGACCCAC GGCTATCTTG GACTCAACTG TAAGGGTCTA
7051 GGGGGCTGGT GTCCCCCCTT TCTGACCTTT GGCCTGTATT TGAGCATTAA
7101 ACTTCACTGA CTAGGTGACC AGTTCCTGAC TTCACTCCAG ATTTTGATTC
7151 TGTCCTCTGG AAAATGGGCT GCTTTAAAGA CACTTCTGGA CCCCCAGAAG
7201 TACCGACACT CCCTATCCTT CATAAACCAG CCTGGGTGCC CGGTGCAGTG
7251 GCTCATGCCT GTAATCCCAA CACTTTGAGA GGCCGAGGCG GGTGGGTCAC
7301 CTGAGGTCAG GAGTTCGAGA CCAGCCTGGC CAACATGGTG AAACCCCGTC
7351 TCTACTAAAA AATAAAATAT GAAAATTAGC CGTGCATGGT GGTGCATCCT
7401 GTAATCATAG CTACTTGGGA GGTTGAGGCA GGAGAATCGC TTGAACCTGG
7451 GAGGCGAAGG TTGCAGTGAG CCAAGATTGC ACCATTGAAC TCCAGCCTGG
7501 GCAACAAGAG CAAAACTCCA TCTCAATCAA TCAATCAATA AAAAAATAAG
7551 AAAATAAACC AGCCTGGGCT AGAGGAGAAT TCGAGATGGC CAGTCTCGAG
7601 ATCTGAGACC TTGTCATGAT TTTAGCCCAG CAGGTGGAAT ACCTGGTCAG
7651 GAAGAAGCAC ATCTATATCC CCAAGAACGG TCAGATTAAC TTCAGCTGTA
7701 TCAATGCCAA CAACATAAAT TACATCACTG AGGGCATCAA TGAGGCTGTC
7751 CTCCTCACAG AGAGCTCAGA GATGTGTCTT CCAAAGGAAA AAAAACACT
7801 GATTGGAATA AAACTTTAGT CTTTGCAAAA ATCTTGTGCT GATTATTCAT
7851 TACTACAATT CATTTCTTTG CTTATTTATG AAGCAGTGGT CTGGCCTCAG
7901 TACAGAGAAA GAGACAGAGA GAAAGAGAGA GAGAAAGGCC CAGAGGGGAA
7951 GGGTGTATCT ACCTTCATTG GCCATCTCAT ATTTATTGAG CACCTACTAC
8001 ATTAAGGCCC TGAGCTGGCC GTGAAAGGGA GTACAAAAAA CAGGTAGAAA
8051 CCAGCCTGTT TTCTCCAGAC ACTTACAGTC TAGTTGGGAG ACAAGCCTTA
8101 GTCACATAAA ACACTTAAGT AACATTTTAA GGCTGAATGT GACAGAAGTC
8151 AGAATATATA AACAGAAAAT GTGCCAGGAA TTTAGAAAAG AAATACGTCA
8201 AAGTGGGCCA GAATAGATGG GGAGCATCTC ATGAGGAGGT AGCACTTGAT
8251 TGGGATATTG ATAGACAGAT GAATGGATTG GATGAATAAT AACTAATAGA
8301 AGCTGGAAGG ATATCCTAGG TCAATAACAA CCTGAGCAAG TGTCACTGAC
8351 ATGATAAGAA AAAATAAATG TTTATCGGGC AGCTACTAAT ACATGGGACT
8401 CTGCAAACTC CCAGGATACC AACAGGTATA TGACACAGTT GGTGCCCTCC
8451 ACTCTCGTTG GGGAGACACA ATTTATATGG TTGAAAGGAA AAACTCTTTT
8501 TTCTCTCTCC TCTACTGTGA TTCTCAATTC TGACACCAGA TTGTATAGGG
8551 TTTTTCCCAC ACAATTAATT CCGTTCTTTG GTAGACATCA GTTGGGTGTC
8601 TTAAAATTCA ATAGATTCTT TTTTATTTTT TCTTTTCTTG GGATGGCGTC
8651 TCTGTCGCCC AGGCTGCAGT GCAGTTGTGC AATCTCAGCT CACTGCAACT
8701 GCCACCTCCC AGGTTCAAGA GATTCTCTTG CCTCAGTCTC CCAAGTAGCT
8751 GGGACTACAG GTATGTGCCA CCACGCCCGG CTAATTTTTG TATTTTTGTT
8801 AGAGACGGGG TTTCGCCATG TTGGCAGGT TGGTCTTGGA CTCCTCTTCT
8851 CAGGTGATCC ACCCGCCTCA GCCTCTGAAA ATGCCGGGAT TACAGGCGTG
8901 AACCACCATG CCCAGCCCAA TTCAATAGAT TCTGATACTA CCTACCTGGA
8951 GTTAGCATCA AATTCCAGAG GTGAATGGCT CAGTTCTGCA AGACTGCACC
9001 CCGTGAATGC CTCAGTTCTG CAAGACTGCA CCCCACTTCA GATGCCAGTC
9051 ACATGTCCAG TGGTGTGACT TGTGCATCTG CTATAAACTG GGGTTCCTAC
9101 CACTCCTTCC TTGGGTTTGA TAATTTGCCA GAACAATTCA CATATCTCAG
9151 GAAAATAGTT TATTTACTAG ATTATCAGTT TGTTATAAAA GGATGCAACT
9201 CAGGAACAGC CAGATGGAAG ACACGCATAG GGAAAGGGGC GTGGAGCTTC
9251 CATGGTCTCT CTGGGTTCGC CCTCCCAGCT CCTCCATATG TTCAGCAACC
```

FIGURE 3C

```
9301  TGGAAGCTCT CCCAAACCCT TTAGTTAGGG GTTTTTATGA AGGCTTCATT
9351  GCACAGGCAT GATGGACTAA AACATTG    (SEQ ID NO:3)
```

FEATURES:

| | |
|---|---|
| Start: | 2078 |
| Exon: | 2078-2192 |
| Intron: | 2193-3230 |
| Exon: | 3231-3412 |
| Intron: | 3413-4362 |
| Exon: | 4363-4474 |
| Intron: | 4475-4725 |
| Exon: | 4726-4835 |
| Intron: | 4836-5054 |
| Exon: | 5055-5147 |
| Intron: | 5148-5241 |
| Exon: | 5242-5392 |
| Intron: | 5393-6242 |
| Exon: | 6243-6408 |
| Intron: | 6409-6896 |
| Exon: | 6897-7107 |
| Stop: | 7108 |

CHROMOSOME MAP POSITION:
Chromosome 8

ALLELIC VARIANTS (SNPs):

| DNA Position | Major | Minor | Domain | Protein Position | Major | Minor |
|---|---|---|---|---|---|---|
| 1563 | - | T | Beyond ORF(5') | | | |
| 3018 | G | A | Intron | | | |
| 4196 | G | C | Intron | | | |
| 4197 | G | A | Intron | | | |
| 4289 | G | A | Intron | | | |
| 6965 | A | G | Exon | 333 | Q | R |
| 7065 | C | T | Exon | 366 | P | P |
| 8521 | T | C | Beyond ORF(3') | | | |

Context:

DNA
Position

```
1563    CCAAAAAAAGAAAGAAAAAGAAACTTAACAAACATATGTAGAAGTCTTGGCTCTAGATAA
        CTGAGAGAAATAGGACTGGCTTAGTGAGTTGCCAATTATATTCTAATAATAGGATTCTTT
        ATTAAAACAACTGTGGAAGAAAACAGTGTTTGCTTTTTATTCCTTTTGAAATCTGGGGCA
        CTTTGCAAAATGGAAATCAATGCCTCGACTTGCATTGGTGTGTGATCTGGGGTTTTTGCT
        TCTGCAGGAGAAGCCCTATCTGGCTTATTGGCTGCCTGCCTTGCCCTATGTCTTTCTTTC
        [-,T]
        TTTTTTTTTTTTTTAATTTGTATAAATGTGTGAAGTACAAGTGTAATTTTGTTAGATGCAT
        ACATCGCATAGTGGTGAAGTCAGGGCTTTTAGGGTATCCATAACCCCAACAATGTACATT
        GTATCTGTTAAGTAATCTCCCATTATCCTTGCCCTGTCATCTAAGGAGTGGGCTTGTTAC
        TTTGGACTGAGCCACCTGGGGCTAGAGAAGAGAAGGCATTGAGTGAGGGAAACGGGCTTG
        GGAATTCCGGAGATTGTTATCCTGCCCTGCCCGCTGTCTGAGGGGATTCTCCTCAAGTAC

3018    TGCCCAGGCTGAAGTGCAGTGGCAAGGATCTCAGCTCACTGCCACCTTTGCCTCCTGGGC
        TCAAACCATCCTCTTGCCTCAGCCTCCTGAGTAGCTGGGACTACAGGCGCTGGTCACCAT
        GTCTGGCTGTTTTGTATTTTTTTGTAGAGACAGGGTTTCATCATGTTGCCCAGGCTGATC
        TTGAACTCCTGAACTCAAGTGATCCACCCACCTTAGCCTCCCGAAGTGCTGGGATTACAG
        GCCTGAGCCACCAATCCTGGGCTTGTATGATTTTTAACCTTTAAAATGGCATAGGTTTCA
        [G,A]
        TTGTCTTTTTTAAAAAGACAAAAATAATACACATTCACTAACAGCATATTCTTTTCATCA
        AGGAGAAAAGAAAAGGGAAAGTTGTATTTTCACAGGCACCTTCCCACAGCCCCATGGAGT
```

FIGURE 3D

```
         CCAGGAGAGATTTGTTTGCAGGCTGTCTGCAGAGCTCAGCCCTGGGGGCCCAAACCAGGC
         ATCTGGAGCTCCCTCTGTGGTTTTCCTCACAGTCTGCATGACAAATGAAGGCCATCCCTG
         GGTTTCTCTCGTGGTGCAGAAGACTCGACTACAGATTTCACAGGATCCCTCCCTGAATTA

4196     CCATGTTGGCCAGGCTGGTCTCAAACTCCTGGCCTCAGGGGATTCCCTGCCTCGTCCTCC
         CAAAGTGCTGGGATTACAGGCATGAGCTACTGCGTCTCGCCTCCATTACTGTTTTAGAGT
         GTTATTTCTGTCTATTTCTTTTTATTTTTTAATGTTTATTTACTTATTATTTTTTTGAGA
         CGGAGTCTCACTCTGTCACCCAGACTGGAGTGCAGTGGCCTGATCTCCGCTCACTGCAAC
         TTCCGCCTTCCGGGTTCAAGTGATTCTCCTGCCTCAGCCTCTTGAGTAGCGGGGATTACA
         [G,C]
         GTGCCCAACACCACATCCGGCTAATTTTTGTATTTTTAGTAGATACGGGGTTTCAACATG
         TTGGCCATGACCTCGAGTGATCCACCCACCCCGGCCTCCCAAAGTGCTGGAATTACAGGT
         GTGAGCCACCACACCTGGCCTATTTGTGTCTATGTCTTGCTGGCAGGTAGGGGGTGTACA
         CACTGTTGGTGACAGTGGTGCCTTCCAGCTTGGCGTCCAGTTTCTCAGAGCTTGGCATAA
         GGATGCTCGTATAGTTTACATCATCTCTTCTCAAAAAGGTTAGTCTTACCCAAGATGAGG

4197     CATGTTGGCCAGGCTGGTCTCAAACTCCTGGCCTCAGGGGATTCCCTGCCTCGTCCTCCC
         AAAGTGCTGGGATTACAGGCATGAGCTACTGCGTCTCGCCTCCATTACTGTTTTAGAGTG
         TTATTTCTGTCTATTTCTTTTTATTTTTTAATGTTTATTTACTTATTATTTTTTTGAGAC
         GGAGTCTCACTCTGTCACCCAGACTGGAGTGCAGTGGCCTGATCTCCGCTCACTGCAACT
         TCCGCCTTCCGGGTTCAAGTGATTCTCCTGCCTCAGCCTCTTGAGTAGCGGGGATTACAG
         [G,A]
         TGCCCAACACCACATCCGGCTAATTTTTGTATTTTTAGTAGATACGGGGTTTCAACATGT
         TGGCCATGACCTCGAGTGATCCACCCACCCCGGCCTCCCAAAGTGCTGGAATTACAGGTG
         TGAGCCACCACACCTGGCCTATTTGTGTCTATGTCTTGCTGGCAGGTAGGGGTGTACAC
         ACTGTTGGTGACAGTGGTGCCTTCCAGCTTGGCGTCCAGTTTCTCAGAGCTTGGCATAAG
         GATGCTCGTATAGTTTACATCATCTCTTCTCAAAAAGGTTAGTCTTACCCAAGATGAGGG

4289     GTCTCGCCTCCATTACTGTTTTAGAGTGTTATTTCTGTCTATTTCTTTTTATTTTTTAAT
         GTTTATTTACTTATTATTTTTTGAGACGGAGTCTCACTCTGTCACCCAGACTGGAGTGC
         AGTGGCCTGATCTCCGCTCACTGCAACTTCCGCCTTCCGGGTTCAAGTGATTCTCCTGCC
         TCAGCCTCTTGAGTAGCGGGGATTACAGGTGCCCAACACCACATCCGGCTAATTTTTGTA
         TTTTTAGTAGATACGGGGTTTCAACATGTTGGCCATGACCTCGAGTGATCCACCCACCCC
         [G,A]
         GCCTCCCAAAGTGCTGGAATTACAGGTGTGAGCCACCACACCTGGCCTATTTGTGTCTAT
         GTCTTGCTGGCAGGTAGGGGGTGTACACACTGTTGGTGACAGTGGTGCCTTCCAGCTTGG
         CGTCCAGTTTCTCAGAGCTTGGCATAAGGATGCTCGTATAGTTTACATCATCTCTTCTCA
         AAAAGGTTAGTCTTACCCAAGATGAGGGGAACAGCAATCCCCGTCCCTTGTTCCTAATCC
         TCACCCCATTTGCCATCTTCACTGTTATCCCTCATTCTCTGTCATGAGCAAAATGGCAGA

6965     GGGGAGATAAGAGAGCATCAGGGGCTTGCAACTCTGGCAAAATCTGCCTGGGAGCCTCCC
         TGGTTTGCTTAAATGAATATGAGATCAAACCTCCCTCCCACTCATAATCATCCCAGAGCC
         TCTGGCACTCTGTTGGAGACCTTTGAAGGTAAGAAGAGTGGACTGGCAATGAGGGAGGTT
         TGAGGGCAAGGGGGACCTCACACCCTCCTTTCTCATTGTCCTTCCTTGGTAGGAAGCAGA
         GTCTAAAAGAAGTTGTAGAGAACATCATGCTAACCAAGGAAAAAGTGAAGGAGAAACTCC
         [A,G]
         GCTCCTGGGAACCCCTGGGTCCTGGGGTCACATCACCGAGCAGAGTGGGACCCACGGCTA
         TCTTGGACTCAACTGTAAGGGTCTAGGGGGCTGGTGTCCCCCCTTTCTGACCTTTGGCCT
         GTATTTGAGCATTAAACTTCACTGACTAGGTGACCAGTTCCTAGCTTCACTCCAGATTTT
         GATTCTGTCCTCTGGAAAATGGGCTGCTTTAAAGACACTTCTGGACCCCAGAAGTACCG
         ACACTCCCTATCCTTCATAAACCAGCCTGGGTGCCCGGTGCAGTGGCTCATGCCTGTAAT

7065     CTCATAATCATCCCAGAGCCTCTGGCACTCTGTTGGAGACCTTTGAAGGTAAGAAGAGTG
         GACTGGCAATGAGGGAGGTTTGAGGGCAAGGGGGACCTCACACCCTCCTTTCTCATTGTC
         CTTCCTTGGTAGGAAGCAGAGTCTAAAAGAAGTTGTAGAGAACATCATGCTAACCAAGGA
         AAAAGTGAAGGAGAAACTCCAGCTCCTGGGAACCCCTGGGTCCTGGGGTCACATCACCGA
         GCAGAGTGGGACCCACGGCTATCTTGGACTCAACTGTAAGGGTCTAGGGGGCTGGTGTCC
         [C,T]
         CCCTTTCTGACCTTTGGCCTGTATTTGAGCATTAAACTTCACTGACTAGGTGACCAGTTC
         CTAGCTTCACTCCAGATTTTGATTCTGTCCTCTGGAAAATGGGCTGCTTTAAAGACACTT
         CTGGACCCCAGAAGTACCGACACTCCCTATCCTTCATAAACCAGCCTGGGTGCCCGGTG
         CAGTGGCTCATGCCTGTAATCCCAACACTTTGAGAGGCCGAGGCGGGTGGGTCACCTGAG
```

FIGURE 3E

```
           GTCAGGAGTTCGAGACCAGCCTGGCCAACATGGTGAAACCCCGTCTCTACTAAAAAATAA
8521       GGAGCATCTCATGAGGAGGTAGCACTTGATTGGGATATTGATAGACAGATGAATGGATTG
           GATGAATAATAACTAATAGAAGCTGGAAGGATATCCTAGGTCAATAACAACCTGAGCAAG
           TGTCACTGACATGATAAGAAAAAATAAATGTTTATCGGGCAGCTACTAATACATGGGACT
           CTGCAAACTCCCAGGATACCAACAGGTATATGACACAGTTGGTGCCCTCCACTCTCGTTG
           GGGAGACACAATTTATATGGTTGAAAGGAAAAACTCTTTTTTCTCTCTCCTCTACTGTGA
           [T,C]
           TCTCAATTCTGACACCAGATTGTATAGGGTTTTTCCCACACAATTAATTCCGTTCTTTGG
           TAGACATCAGTTGGGTGTCTTAAAATTCAATAGATTCTTTTTTATTTTTTCTTTTCTTGG
           GATGGCGTCTCTGTCGCCCAGGCTGCAGTGCAGTTGTGCAATCTCAGCTCACTGCAACTG
           CCACCTCCCAGGTTCAAGAGATTCTCTTGCCTCAGTCTCCCAAGTAGCTGGGACTACAGG
           TATGTGCCACCACGCCCGGCTAATTTTTGTATTTTTGTTAGAGACGGGGTTTCGCCATGT
```

FIGURE 3F

ISOLATED NUCLEIC ACID MOLECULES ENCODING HUMAN ASPARTATE AMINOTRANSFERASE PROTEIN AND USES THEREOF

RELATED APPLICATIONS

The present application claims priority to provisional application U.S. Serial No. 60/207,350, filed May 30, 2000 (Atty. Docket CL000615-PROV).

FIELD OF THE INVENTION

The present invention is in the field of aminotransferase proteins that are related to the aspartate aminotransferase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Aminotransferases

Aminotransferases are enzymes that catalyze the transfer of amino groups from .alpha.-amino to .alpha.-keto acids. They are also called transaminases. The alpha.-amino groups of the 20 L-amino acids commonly found in proteins are removed during the oxidative degradation of the amino acids. The removal of the .alpha.-amino groups, the first step in the catabolism of most of the L-amino acids, is promoted by aminotransferases (or transaminases). In these transamination reactions, the .alpha.-amino group is transferred to the .alpha.-carbon atom of .alpha.-ketoglutarate, leaving behind the corresponding .alpha.-keto acid analog of the amino acid. There is no net deamination (i.e., loss of amino groups) in such reactions because the .alpha.-ketoglutarate becomes aminated as the .alpha.-amino acid is deaminated. The effect of transamination reactions is to collect the amino groups from many different amino acids in the form of only one, namely, L-glutamate. The glutamate channels amino groups either into biosynthetic pathways or into a final sequence of reactions by which nitrogenous waste products are formed and then excreted.

Cells contain several different aminotransferases, many specific for .alpha.-ketoglutarate as the amino group acceptor. The aminotransferases differ in their specificity for the other substrate, the L-amino acid that donates the amino group, and are named for the amino group donor. The reactions catalyzed by the aminotransferases are freely reversible, having an equilibrium constant of about 1.0 (.DELTA.G.sup.0'.congruent.0 kJ/mol).

Aminotransferases are classic examples of enzymes catalyzing bimolecular ping-pong reactions. In such reactions the first substrate must leave the active site before the second substrate can bind. Thus the incoming amino acid binds to the active site, donates its amino group to pyridoxal phosphate, and departs in the form of an .alpha.-keto acid. Then the incoming .alpha.-keto acid is bound, accepts the amino group from pyridoxamine phosphate, and departs in the form of an amino acid.

The measurement of alanine aminotransferase and aspartate aminotransferase levels in blood serum is an important diagnostic procedure in medicine, used as an indicator of damage to the heart and other organs and to monitor recovery from the damage. For example, measurement of aspartate aminotransferase isoenzymes is used to determine the extent of liver necrosis and for determining prognosis in hepatic disease, as well as for diagnosing active alcoholic liver disease. Measurement of aspartate aminotransferase isoenzymes in acute myocardial infarction provides additional diagnostic information not provided by other tests used in the art, such as creatine kinase and lactate dehydrogenase-based tests (Panteghini, Clin. Biochem. 23 (4), 311–319 (1990)).

Several heart and liver diseases have been correlated with abnormally high levels of serum aspartate transaminase (AST). Examples of such conditions include acute myocardial infarction, pulmonary emulsion, acute pancreatitis, viral and toxic hepatitis, and acute cirrhosis. Generally speaking, AST is elevated in diseases affecting tissues rich in AST.

Extensive studies have shown that 92–98% of patients with acute myocardial infarction have elevated serum AST level. The measured levels are usually four to ten times the upper limit of normal values. The elevated AST levels develop six to twelve hours after the time of infarction and usually return to normal by the third or fourth day. Secondary rises can be correlated with other features, suggesting extension or recurrence of myocardial infarction. Also, mild elevations of serum AST levels have been reported in patients with pulmonary infarction. In patients with congestive heart failure and those with marked tachycardia, mild to moderate degrees of AST elevation may occur. These have been attributed to hepatic necrosis secondary to hepatic congestion. Patients with pericarditis also have been reported to have a fifty percent incidence of slightly elevated AST levels.

Striking elevations in AST levels are observed in the serum of almost all patients with acute hepatic necrosis. In patients with cirrhosis of the liver there is a 60–70% incidence of elevated AST levels. Obviously the early detection of an abnormal rise in AST levels can lead to more rapid and accurate diagnosis of heart and liver disease.

Elevated AST levels have even been correlated with various cancers. Approximately half the patients with metastatic carcinoma have elevated serum AST levels in the same range as patients with cirrhosis and posthepatic jaundice. Less frequently such moderately elevated AST levels are observed in patients with lymphoma and leukeumia. See, Todd-Sanford, Clinical Diagnosis By Laboratory Methods, W. B. Saunders Co., 14th Ed., pp. 693–723 (1969).

Accordingly, the identification of a new member of the aminotransferase family of proteins, particularly one related to the aspartate aminotransferase, provide targets for examining protein turnover in response to a pathological or biological process.

SUMMARY OF THE INVENTION

The present invention is based in part on the identification of amino acid sequences of human aminotransferase peptides and proteins that are related to the aspartate aminotransferase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate aminotransferase activity in cells and tissues that express the aminotransferase. Experimental data as provided in FIG. 1 indicates expression in humans in the testis.

DESCRIPTION OF THE FIGURE SHEETS

FIG. 1 provides the nucleotide sequence of a cDNA molecule that encodes the aminotransferase protein of the present invention. In addition structure and functional information is provided, such as ATG start, stop and tissue distribution, where available, that allows one to readily determine specific uses of inventions based on this molecular sequence. Experimental data as provided in FIG. 1 indicates expression in humans in the testis.

FIG. 2 provides the predicted amino acid sequence of the aminotransferase of the present invention. In addition structure and functional information, such as protein family and function, modification sites, is provided that allows one to readily determine specific uses of inventions based on this molecular sequence.

FIG. 3 provides genomic sequences that span the gene encoding the aminotransferase protein of the present invention. In addition structure and functional information, such as intron/exon structure, promoter location, etc., is provided that allows one to readily determine specific uses of inventions based on this molecular sequence. As illustrated in FIG. 3, SNPs were identified at 8 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a aminotransferase protein or part of a aminotransferase protein and are related to the aspartate aminotransferase subfamily. Utilizing these sequences, additional genomic sequences were assembled and transcript and/or cDNA sequences were isolated and characterized. Based on this analysis, the present invention provides amino acid sequences of human aminotransferase peptides and proteins that are related to the aspartate aminotransferase subfamily, nucleic acid sequences in the form of transcript sequences, cDNA sequences and/or genomic sequences that encode these aminotransferase peptides and proteins, nucleic acid variation (allelic information), tissue distribution of expression, and information about the closest art known protein/peptide/domain that has structural or sequence homology to the aminotransferase of the present invention.

In addition to being previously unknown, the peptides that are provided in the present invention are selected based on their ability to be used for the development of commercially important products and services. Specifically, the present peptides are selected based on homology and/or structural relatedness to known aminotransferase proteins of the aspartate aminotransferase subfamily and the expression pattern observed. Experimental data as provided in FIG. 1 indicates expression in humans in the testis. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the know aspartate family or subfamily of aminotransferase proteins.

Specific Embodiments

Peptide Molecules

The present invention provides nucleic acid sequences that encode protein molecules that have been identified as being members of the aminotransferase family of proteins and are related to the aspartate aminotransferase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the aminotransferase peptides of the present invention, aminotransferase peptides, or peptides/proteins of the present invention.

The present invention provides isolated peptide and protein molecules that consist of, consist essentially of or are comprised of the amino acid sequences of the aminotransferase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the aminotransferase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated aminotransferase peptide can be purified from cells that naturally express it, purified from cells that have been altered to express it (recombinant), or synthesized using known protein synthesis methods. Experimental data as provided in FIG. 1 indicates expression in humans in the testis. For example, a nucleic acid molecule encoding the aminotransferase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequences that such a protein is consists of is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that are comprised of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein is comprised of an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the aminotransferase peptides of the present invention are the naturally occurring mature proteins. A brief description of how various types of these proteins can be made/isolated is provided below.

The aminotransferase peptides of the present invention can be attached to heterologous sequences to form chimeric or fusion proteins. Such chimeric and fusion proteins comprise a aminotransferase peptide operatively linked to a heterologous protein having an amino acid sequence not substantially homologous to the aminotransferase peptide. "Operatively linked" indicates that the aminotransferase peptide and the heterologous protein are fused in-frame. The heterologous protein can be fused to the N-terminus or C-terminus of the aminotransferase peptide.

In some uses, the fusion protein does not affect the activity of the aminotransferase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant aminotransferase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A aminotransferase peptide-encoding nucleic acid can be cloned into such an expression vector such that the fusion moiety is linked in-frame to the aminotransferase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the aminotransferase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the aminotransferase peptides of the present invention as well as being encoded by the same genetic locus as the aminotransferase peptide provided herein. The gene encoding the novel aminotransferase protein of the present invention is located on a genome component that has been mapped to human chromosome 8 (as indicated in FIG. 3), which is supported by multiple lines of evidence, such as STS and BAC map data.

Allelic variants of a aminotransferase peptide can readily be identified as being a human protein having a high degree (significant) of sequence homology/identity to at least a portion of the aminotransferase peptide as well as being encoded by the same genetic locus as the aminotransferase peptide provided herein. Genetic locus can readily be determined based on the genomic information provided in FIG. 3, such as the genomic sequence mapped to the reference human. The gene encoding the novel aminotransferase protein of the present invention is located on a genome component that has been mapped to human chromosome 8 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a aminotransferase peptide encoding nucleic acid molecule under stringent conditions as more fully described below.

FIG. 3 provides information on SNPs that have been found in the gene encoding the aminotransferase protein of the present invention. SNPs were identified at 8 different nucleotide positions, including a non-synonymous coding SNP at position 6965 (protein position 333). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect control/regulatory elements.

Paralogs of a aminotransferase peptide can readily be identified as having some degree of significant sequence homology/identity to at least a portion of the aminotransferase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a aminotransferase peptide encoding nucleic acid molecule under moderate to stringent conditions as more fully described below.

Orthologs of a aminotransferase peptide can readily be identified as having some degree of significant sequence homology/identity to at least a portion of the aminotransferase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a aminotransferase peptide encoding nucleic acid molecule under moderate to stringent conditions, as more fully described below, depending on the degree of relatedness of the two organisms yielding the proteins.

Non-naturally occurring variants of the aminotransferase peptides of the present invention can readily be generated using recombinant techniques. Such variants include, but are not limited to deletions, additions and substitutions in the amino acid sequence of the aminotransferase peptide. For example, one class of substitutions are conserved amino acid substitution. Such substitutions are those that substitute a given amino acid in a aminotransferase peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

Variant aminotransferase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as aminotransferase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the aminotransferase peptides, in addition to proteins and peptides that comprise and consist of such fragments, particularly those comprising the residues identified in FIG. 2). The fragments to which the invention pertains, however, are not to be construed as encompassing fragments that may be disclosed publicly prior to the present invention.

As used herein, a fragment comprises at least 8 10, 12, 14, 16 or more contiguous amino acid residues from a aminotransferase peptide. Such fragments can be chosen based on the ability to retain one or more of the biological activities of the aminotransferase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the aminotransferase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in aminotransferase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Accordingly, the aminotransferase peptides of the present invention also encompass derivatives or analogs in which a substituted amino acid residue is not one encoded by the genetic code, in which a substituent group is included, in which the mature aminotransferase peptide is fused with another compound, such as a compound to increase the half-life of the aminotransferase peptide (for example, polyethylene glycol), or in which the additional amino acids are fused to the mature aminotransferase peptide, such as a leader or secretory sequence or a sequence for purification of the mature aminotransferase peptide or a pro-protein sequence.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a aminotransferase-effector protein interaction or aminotransferase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, aminotransferases isolated from humans and their human/mammalian orthologs serve as targets for identifying agents for use in mammalian therapeutic applications, e.g. a human drug, particularly in modulating a biological or pathological response in a cell or tissue that expresses the aminotransferase. Experimental data as provided in FIG. 1 indicates that the aminotransferase proteins of the present invention are expressed in humans in the testis, as indicated by virtual northern blot analysis and PCR-based tissue screening panels. A large percentage of pharmaceutical agents are being developed that modulate the activity of aminotransferase proteins, particularly members of the aspartate subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the testis. Such uses can readily be determined using the information provided herein, that known in the art and routine experimentation.

The aminotransferase polypeptides (including variants and fragments that may have been disclosed prior to the present invention) are useful for biological assays related to aminotransferases that are related to members of the aspartate subfamily. Such assays involve any of the known aminotransferase functions or activities or properties useful for diagnosis and treatment of aminotransferase-related conditions that are specific for the subfamily of aminotransferases that the one of the present invention belongs to, particularly in cells and tissues that express the aminotransferase. Experimental data as provided in FIG. 1 indicates that the aminotransferase proteins of the present invention are expressed in humans in the testis, as indicated by virtual northern blot analysis and PCR-based tissue screening panels.

The aminotransferase polypeptides are also useful in drug screening assays, in cell-based or cell-free systems. Cell-based systems can be native, i.e., cells that normally express the aminotransferase, as a biopsy or expanded in cell culture. Experimental data as provided in FIG. 1 indicates expression in humans in the testis. In an alternate embodiment, cell-based assays involve recombinant host cells expressing the aminotransferase protein.

The polypeptides can be used to identify compounds that modulate aminotransferase activity of the protein in its natural state or an altered form that causes a specific disease or pathology associated with the aminotransferase. Both the aminotransferases of the present invention and appropriate variants and fragments can be used in high-throughput screens to assay candidate compounds for the ability to bind to the aminotransferase. These compounds can be further screened against a functional aminotransferase to determine the effect of the compound on the aminotransferase activity. Further, these compounds can be tested in animal or invertebrate systems to determine activity/effectiveness. Compounds can be identified that activate (agonist) or inactivate (antagonist) the aminotransferase to a desired degree.

Further, the aminotransferase polypeptides can be used to screen a compound for the ability to stimulate or inhibit interaction between the aminotransferase protein and a molecule that normally interacts with the aminotransferase protein, e.g. a substrate or a component of the signal pathway that the aminotransferase protein normally interacts (for example, another aminotransferase). Such assays typically include the steps of combining the aminotransferase protein with a candidate compound under conditions that allow the aminotransferase protein, or fragment, to interact with the target molecule, and to detect the formation of a complex between the protein and the target or to detect the biochemical consequence of the interaction with the aminotransferase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant aminotransferases or appropriate fragments containing mutations that affect aminotransferase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) aminotransferase activity. The assays typically involve an assay of events in the signal transduction pathway that indicate aminotransferase activity. Thus, the phosphorylation of a substrate, activation of a protein, a change in the expression of genes that are up- or down-regulated in response to the aminotransferase protein dependent signal cascade can be assayed.

Any of the biological or biochemical functions mediated by the aminotransferase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the aminotransferase can be assayed. Experimental data as provided in FIG. 1 indicates that the aminotransferase proteins of the present invention are expressed in humans in the testis, as indicated by virtual northern blot analysis and PCR-based tissue screening panels.

Binding and/or activating compounds can also be screened by using chimeric aminotransferase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native aminotransferase. Accordingly, a different set of signal transduction components is available as an endpoint assay for activation. This allows for assays to be performed in other than the specific host cell from which the aminotransferase is derived.

The aminotransferase polypeptides are also useful in competition binding assays in methods designed to discover compounds that interact with the aminotransferase (e.g. binding partners and/or ligands). Thus, a compound is exposed to a aminotransferase polypeptide under conditions that allow the compound to bind or to otherwise interact with the polypeptide. Soluble aminotransferase polypeptide is also added to the mixture. If the test compound interacts with the soluble aminotransferase polypeptide, it decreases the amount of complex formed or activity from the aminotransferase target. This type of assay is particularly useful in cases in which compounds are sought that interact with specific regions of the aminotransferase. Thus, the soluble polypeptide that competes with the target aminotransferase region is designed to contain peptide sequences corresponding to the region of interest.

To perform cell free drug screening assays, it is sometimes desirable to immobilize either the aminotransferase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of aminotransferase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a aminotransferase-binding protein and a candidate compound are incubated in the aminotransferase protein-presenting wells and the amount of complex trapped in the well can be quantitated. Methods for detecting such complexes, in addition to those described above for the GST-immobilized complexes, include immunodetection of complexes using antibodies reactive with the aminotransferase protein target molecule, or which are reactive with aminotransferase protein and compete with the target molecule, as well as enzyme-linked assays which rely on detecting an enzymatic activity associated with the target molecule.

Agents that modulate one of the aminotransferases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of aminotransferase protein activity identified according to these drug screening assays can be used to treat a subject with a disorder mediated by the aminotransferase pathway, by treating cells or tissues that express the aminotransferase. Experimental data as provided in FIG. 1 indicates expression in humans in the testis. These methods of treatment include the steps of administering a modulator of aminotransferase activity in a pharmaceutical composition to a subject in need of such treatment, the modulator being identified as described herein.

In yet another aspect of the invention, the aminotransferase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the aminotransferase and are involved in aminotransferase activity. Such aminotransferase-binding proteins are also likely to be involved in the propagation of signals by the aminotransferase proteins or aminotransferase targets as, for example, downstream elements of a aminotransferase-mediated signaling pathway. Alternatively, such aminotransferase-binding proteins are likely to be aminotransferase inhibitors.

The two-hybrid system is based on the modular nature of most transcription factors, which consist of separable DNA-binding and activation domains. Briefly, the assay utilizes two different DNA constructs. In one construct, the gene that codes for a aminotransferase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a aminotransferase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the aminotransferase protein.

This invention further pertains to novel agents identified by the above-described screening assays. Accordingly, it is within the scope of this invention to further use an agent identified as described herein in an appropriate animal model. For example, an agent identified as described herein (e.g., a aminotransferase-modulating agent, an antisense aminotransferase nucleic acid molecule, a aminotransferase-specific antibody, or a aminotransferase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The aminotransferase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the testis. The method involves contacting a biological sample with a compound capable of interacting with the aminotransferase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered aminotransferase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the aminotransferase protein in which one or more of the aminotransferase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and aminotransferase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the testis. Accordingly, methods for treatment include the use of the aminotransferase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the aminotransferase proteins. Antibodies can be prepared from any region of the peptide as described herein. However, preferred regions will include those involved in function/activity and/or aminotransferase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the aminotransferase proteins of the present invention are expressed in humans in the testis, as indicated by virtual northern blot analysis and PCR-based tissue screening panels. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the testis. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the testis. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the testis. Thus, where a specific protein has been correlated with expression in a specific tissue, antibodies that are specific for this protein can be used to identify a tissue type.

The antibodies are also useful for inhibiting protein function, for example, blocking the binding of the aminotransferase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array.

Nucleic Acid Molecules

The present invention further provides isolated nucleic acid molecules that encode a aminotransferase peptide or protein of the present invention (cDNA, transcript and genomic sequence). Such nucleic acid molecules will consist of, consist essentially of, or comprise a nucleotide sequence that encodes one of the aminotransferase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that are comprised of the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule is comprised of a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the aminotransferase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the aminotransferase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel aminotransferase protein of the present invention is located on a genome component that has been mapped to human chromosome 8 (as indicated in FIG. 3), which is supported by multiple lines of evidence, such as STS and BAC map data.

FIG. 3 provides information on SNPs that have been found in the gene encoding the aminotransferase protein of the present invention. SNPs were identified at 8 different nucleotide positions, including a non-synonymous coding SNP at position 6965 (protein position 333). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6x sodium chloride/sodium citrate (SSC) at about 45 C., followed by one or more washes in 0.2 × SSC, 0.1% SDS at 50–65C. Examples of moderate to low stringency hybridation conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 8 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel aminotransferase protein of the present invention is located on a genome component that has been mapped to human chromosome 8 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form and distribution of nucleic acid expression. Experimental data as provided in FIG. 1 indicates that the aminotransferase proteins of the present invention are expressed in humans in the testis, as indicated by virtual northern blot analysis and PCR-based tissue screening panels. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in aminotransferase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a aminotransferase protein, such as by measuring a level of a aminotransferase-encoding nucleic acid in a sample of cells from a subject e.g., mRNA or genomic DNA, or determining if a aminotransferase gene has been mutated. Experimental data as provided in FIG. 1 indicates that the aminotransferase proteins of the present invention are expressed in humans in the testis, as indicated by virtual northern blot analysis and PCR-based tissue screening panels.

Nucleic acid expression assays are useful for drug screening to identify compounds that modulate aminotransferase nucleic acid expression.

The invention thus provides a method for identifying a compound that can be used to treat a disorder associated with nucleic acid expression of the aminotransferase gene, particularly biological and pathological processes that are mediated by the aminotransferase in cells and tissues that express it. Experimental data as provided in FIG. 1 indicates expression in humans in the testis. The method typically includes assaying the ability of the compound to modulate the expression of the aminotransferase nucleic acid and thus identifying a compound that can be used to treat a disorder characterized by undesired aminotransferase nucleic acid expression. The assays can be performed in cell-based and cell-free systems. Cell-based assays include cells naturally expressing the aminotransferase nucleic acid or recombinant cells genetically engineered to express specific nucleic acid sequences.

The assay for aminotransferase nucleic acid expression can involve direct assay of nucleic acid levels, such as mRNA levels, or on collateral compounds involved in the signal pathway. Further, the expression of genes that are up- or down-regulated in response to the aminotransferase protein signal pathway can also be assayed. In this embodiment the regulatory regions of these genes can be operably linked to a reporter gene such as luciferase.

Thus, modulators of aminotransferase gene expression can be identified in a method wherein a cell is contacted with a candidate compound and the expression of mRNA determined. The level of expression of aminotransferase mRNA in the presence of the candidate compound is compared to the level of expression of aminotransferase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate aminotransferase nucleic acid expression in cells and tissues that express the aminotransferase. Experimental data as provided in FIG. 1 indicates that the aminotransferase proteins of the present invention are expressed in humans in the testis, as indicated by virtual northern blot analysis and PCR-based tissue screening panels. Modulation includes both up-regulation (i.e. activation or agonization) or down-regulation (suppression or antagonization) or nucleic acid expression.

Alternatively, a modulator for aminotransferase nucleic acid expression can be a small molecule or drug identified using the screening assays described herein as long as the drug or small molecule inhibits the aminotransferase nucleic acid expression in the cells and tissues that express the protein. Experimental data as provided in FIG. 1 indicates expression in humans in the testis.

The nucleic acid molecules are also useful for monitoring the effectiveness of modulating compounds on the expression or activity of the aminotransferase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in aminotransferase nucleic acid expression, and particularly in qualitative changes that lead to pathology. The nucleic acid molecules can be used to detect mutations in aminotransferase genes and gene expression products such as mRNA. The nucleic acid molecules can be used as hybridization probes to detect naturally occurring genetic mutations in the aminotransferase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the aminotransferase gene associated with a dysfunction provides a diagnostic tool for an active disease or susceptibility to disease when the disease results from overexpression, underexpression, or altered expression of a aminotransferase protein.

Individuals carrying mutations in the aminotransferase gene can be detected at the nucleic acid level by a variety of techniques. FIG. 3 provides information on SNPs that have been found in the gene encoding the aminotransferase protein of the present invention. SNPs were identified at 8 different nucleotide positions, including a non-synonymous coding SNP at position 6965 (protein position 333). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect control/regulatory elements. The gene encoding the novel aminotransferase protein of the present invention is located on a genome component that has been mapped to human chromosome 8 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample.

Deletions and insertions can be detected by a change in size of the amplified product compared to the normal genotype. Point mutations can be identified by hybridizing amplified DNA to normal RNA or antisense DNA sequences.

Alternatively, mutations in a aminotransferase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and SI protection or the chemical cleavage method. Furthermore, sequence differences between a mutant aminotransferase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the aminotransferase gene in an individual in order to select an appropriate compound or dosage regimen for treatment. FIG. 3 provides information on SNPs that have been found in the gene encoding the aminotransferase protein of the present invention. SNPs were identified at 8 different nucleotide positions, including a non-synonymous coding SNP at position 6965 (protein position 333). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control aminotransferase gene expression in cells, tissues, and organisms. A DNA antisense nucleic acid molecule is designed to be complementary to a region of the gene involved in transcription, preventing transcription and hence production of aminotransferase protein. An antisense RNA or DNA nucleic acid molecule would hybridize to the mRNA and thus block translation of mRNA into aminotransferase protein.

Alternatively, a class of antisense molecules can be used to inactivate mRNA in order to decrease expression of aminotransferase nucleic acid. Accordingly, these molecules can treat a disorder characterized by abnormal or undesired aminotransferase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the aminotransferase protein, such as substrate binding.

The nucleic acid molecules also provide vectors for gene therapy in patients containing cells that are aberrant in aminotransferase gene expression. Thus, recombinant cells, which include the patient's cells that have been engineered ex vivo and returned to the patient, are introduced into an individual where the cells produce the desired aminotransferase protein to treat the individual.

The invention also encompasses kits for detecting the presence of a aminotransferase nucleic acid in a biological sample. Experimental data as provided in FIG. 1 indicates that the aminotransferase proteins of the present invention are expressed in humans in the testis, as indicated by virtual northern blot analysis and PCR-based tissue screening panels. For example, the kit can comprise reagents such as a labeled or labelable nucleic acid or agent capable of detecting aminotransferase nucleic acid in a biological sample; means for determining the amount of aminotransferase nucleic acid in the sample; and means for comparing the amount of aminotransferase nucleic acid in the sample with a standard. The compound or agent can be packaged in a suitable container. The kit can further comprise instructions for using the kit to detect aminotransferase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the aminotransferase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the aminotransferase gene of the present invention. FIG. 3 provides information on SNPs that have been found in the gene encoding the aminotransferase protein of the present invention. SNPs were identified at 8 different nucleotide positions, including a non-synonymous coding SNP at position 6965 (protein position 333). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified aminotransferase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, or MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroaminotransferase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd,* ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd*, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as aminotransferases, appropriate secretion signals are incorporated into the vector. The signal sequence can be endogenous to the peptides or heterologous to these peptides.

Where the peptide is not secreted into the medium, which is typically the case with aminotransferases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a aminotransferase protein or peptide that can be further purified to produce desired amounts of aminotransferase protein or fragments. Thus, host cells containing expression vectors are useful for peptide production.

Host cells are also useful for conducting cell-based assays involving the aminotransferase protein or aminotransferase protein fragments, such as those described above as well as other formats known in the art. Thus, a recombinant host cell expressing a native aminotransferase protein is useful for assaying compounds that stimulate or inhibit aminotransferase protein function.

Host cells are also useful for identifying aminotransferase protein mutants in which these functions are affected. If the mutants naturally occur and give rise to a pathology, host cells containing the mutations are useful to assay compounds that have a desired effect on the mutant aminotransferase protein (for example, stimulating or inhibiting function) which may not be indicated by their effect on the native aminotransferase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a aminotransferase protein and identifying and evaluating modulators of aminotransferase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the aminotransferase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the aminotransferase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, aminotransferase protein activation, and signal transduction, may not be evident from in vitro cell-free or cell-based assays. Accordingly, it is useful to provide non-human transgenic animals to assay in vivo aminotransferase protein function, including substrate interaction, the effect of specific mutant aminotransferase proteins on aminotransferase protein function and substrate interaction, and the effect of chimeric aminotransferase proteins. It is also possible to assess the effect of null mutations; that is, mutations that substantially or completely eliminate one or more aminotransferase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, a virus, and a bacteriophage.

8. A vector according to claim 2, wherein said isolated nucleic acid molecule is inserted into said vector in proper orientation and correct reading frame such that a polypeptide comprising SEQ ID NO:2 may be expressed by a cell transformed with said vector.

9. A vector according to claim 8, wherein said isolated nucleic acid molecule is operatively linked to a promoter sequence.

10. An isolated nucleic acid molecule comprising a nucleotide sequence selected from the group consisting of:
    (a) a nucleotide sequence that encodes SEQ ID NO:2;
    (b) SEQ ID NO:1;
    (c) residues 78–1217 of SEQ ID NO:1;
    (d) SEQ ID NO:3; and
    (e) a nucleotide sequence that is completely complementary to a nucleotide sequence of (a)–(d).

11. A nucleic acid vector comprising the nucleic acid molecule of claim 10.

12. A host cell containing the vector of claim 11.

13. A process for producing a polypeptide comprising culturing the host cell of claim 12 under conditions sufficient for the production of said polypeptide, and recovering said polypeptide.

14. A vector according to claim 11, wherein said vector is selected from the group consisting of a plasmid, a virus, and a bacteriophage.

15. A vector according to claim 11, wherein said isolated nucleic acid molecule is inserted into said vector in proper orientation and correct reading frame such that a polypeptide comprising SEQ ID NO:2 may be expressed by a cell transformed with said vector.

16. A vector according to claim 15, wherein said isolated nucleic acid molecule is operatively linked to a promoter sequence.

17. An isolated nucleic acid molecule consisting of a nucleotide sequence selected from the group consisting of:
(a) a nucleotide sequence that encodes an amino acid sequence having at least 99% sequence identity to SEQ ID NO:2;
(b) a nucleotide sequence having at least 99% sequence identity to SEQ ID NO:1; and
(c) a nucleotide sequence having at least 99% sequence identity to SEQ ID NO:3.

* * * * *

SEQUENCE LISTING

<160> NUMBER OF SEQ ID NOS: 5

<210> SEQ ID NO 1
<211> LENGTH: 1517
<212> TYPE: DNA
<213> ORGANISM: Human

<400> SEQUENCE: 1

| | | | | | |
|---|---|---|---|---|---|
| cttggaggaa | gacttctggg | cagaagcgga | acacaggagc | agagacacat | agtcttggct | 60 |
| ccagtttcgt | ttcagttatg | cccacccttt | cagtgttcat | ggatgtgccc | ctcgcccaca | 120 |
| agctagaggg | cagcttgtta | aagacctaca | acaagatga | ttacccgaac | aagatattct | 180 |
| tagcctatag | agtctgcatg | acaaatgaag | gccatccctg | ggtttctctc | gtggtgcaga | 240 |
| agactcgact | acagatttca | caggatccct | ccctgaatta | tgagtacttg | cccaccatgg | 300 |
| gcctgaaatc | attcatccag | gcctctctag | cactcctctt | tggaaagcac | agccaagcca | 360 |
| ttgtggagaa | cagggtaggg | ggtgtacaca | ctgttggtga | cagtggtgcc | ttccagcttg | 420 |
| gcgtccagtt | tctcagagct | tggcataagg | atgctcgtat | agtttacatc | atctcttctc | 480 |
| aaaaagaact | gcatggactc | gtcttccagg | acatgggctt | tacagtttat | gaatactctg | 540 |
| tctgggaccc | caagaagcta | tgcatggacc | ccgacatact | cctcaatgtg | gtggagcaga | 600 |
| tcccacatgg | ctgtgtcctt | gtgatgggga | acattatcga | ctgcaagttg | acaccaagtg | 660 |
| ggtgggcaaa | gttgatgtcc | atgataaaga | gcaagcagat | attcccattt | tttgatattc | 720 |
| cctgtcaagg | tttatacacc | agtgacttgg | aagaagatac | tagaatctta | caatactttg | 780 |
| tgtctcaagg | ctttgagttc | ttctgcagcc | agtctctgtc | caagaatttt | ggcatttatg | 840 |
| atgaaggagt | ggggatgcta | gtggtggtgg | cagtcaacaa | ccagcagctg | ctgtgtgtcc | 900 |
| tctcccagct | ggaaggatta | gcccaggccc | tgtggctaaa | ccccccaac | acgggtgcac | 960 |
| gtgtcatcac | ctccatcctc | tgcaaccctg | ctctgctggg | agaatggaag | cagagtctaa | 1020 |
| aagaagttgt | agagaacatc | atgctaacca | aggaaaaagt | gaaggagaaa | ctccagctcc | 1080 |
| tgggaacccc | tgggtcctgg | ggtcacatca | ccgagcagag | tgggacccac | ggctatcttg | 1140 |
| gactcaactg | taagggtcta | gggggctggt | gtccccccctt | tctgaccttt | ggcctgtatt | 1200 |
| tgagcattaa | acttcactga | ctaggtgacc | agttcctagc | ttcactccag | attttgattc | 1260 |
| tgtcctctgg | aaaatgggct | gctttaaaga | cacttctgga | cccccagaag | taccgacact | 1320 |
| ccctatcctt | cataaaccag | cctgggtgcc | cggtgcagtg | gctcatgcct | gtaatcccaa | 1380 |
| cactttgaga | ggccgaggcg | ggtgggtcac | ctgaggtcag | gagttcgaga | ccagcctggc | 1440 |
| caacatggtg | aaaccccgtc | tctactaaaa | aataaaatat | gaaaattaaa | aaaaaaaaa | 1500 |
| aaaaaaaaaa | aaaaaaa | | | | | 1517 |

<210> SEQ ID NO 2
<211> LENGTH: 380
<212> TYPE: PRT
<213> ORGANISM: Human

<400> SEQUENCE: 2

Met Pro Thr Leu Ser Val Phe Met Asp Val Pro Leu Ala His Lys Leu
 1               5                  10                  15

Glu Gly Ser Leu Leu Lys Thr Tyr Lys Gln Asp Asp Tyr Pro Asn Lys
            20                  25                  30

Ile Phe Leu Ala Tyr Arg Val Cys Met Thr Asn Glu Gly His Pro Trp

|  |  |  |  |  |  |  |  | 35 |  |  |  |  |  | 40 |  |  |  |  |  | 45 |  |
|---|---|---|---|---|---|---|---|---|---|---|---|---|---|---|---|---|---|---|---|---|---|

Val Ser Leu Val Val Gln Lys Thr Arg Leu Gln Ile Ser Gln Asp Pro
 50                  55                  60

Ser Leu Asn Tyr Glu Tyr Leu Pro Thr Met Gly Leu Lys Ser Phe Ile
65                  70                  75                  80

Gln Ala Ser Leu Ala Leu Leu Phe Gly Lys His Ser Gln Ala Ile Val
                 85                  90                  95

Glu Asn Arg Val Gly Gly Val His Thr Val Gly Asp Ser Gly Ala Phe
             100                 105                 110

Gln Leu Gly Val Gln Phe Leu Arg Ala Trp His Lys Asp Ala Arg Ile
         115                 120                 125

Val Tyr Ile Ile Ser Ser Gln Lys Glu Leu His Gly Leu Val Phe Gln
130                 135                 140

Asp Met Gly Phe Thr Val Tyr Glu Tyr Ser Val Trp Asp Pro Lys Lys
145                 150                 155                 160

Leu Cys Met Asp Pro Asp Ile Leu Leu Asn Val Val Glu Gln Ile Pro
                165                 170                 175

His Gly Cys Val Leu Val Met Gly Asn Ile Ile Asp Cys Lys Leu Thr
            180                 185                 190

Pro Ser Gly Trp Ala Lys Leu Met Ser Met Ile Lys Ser Lys Gln Ile
        195                 200                 205

Phe Pro Phe Asp Ile Pro Cys Gln Gly Leu Tyr Thr Ser Asp Leu
210                 215                 220

Glu Glu Asp Thr Arg Ile Leu Gln Tyr Phe Val Ser Gln Gly Phe Glu
225                 230                 235                 240

Phe Phe Cys Ser Gln Ser Leu Ser Lys Asn Phe Gly Ile Tyr Asp Glu
                245                 250                 255

Gly Val Gly Met Leu Val Val Ala Val Asn Asn Gln Gln Leu Leu
            260                 265                 270

Cys Val Leu Ser Gln Leu Glu Gly Leu Ala Gln Ala Leu Trp Leu Asn
        275                 280                 285

Pro Pro Asn Thr Gly Ala Arg Val Ile Thr Ser Ile Leu Cys Asn Pro
290                 295                 300

Ala Leu Leu Gly Glu Trp Lys Gln Ser Leu Lys Glu Val Val Glu Asn
305                 310                 315                 320

Ile Met Leu Thr Lys Glu Lys Val Lys Glu Lys Leu Gln Leu Leu Gly
                325                 330                 335

Thr Pro Gly Ser Trp Gly His Ile Thr Glu Gln Ser Gly Thr His Gly
            340                 345                 350

Tyr Leu Gly Leu Asn Cys Lys Gly Leu Gly Gly Trp Cys Pro Pro Phe
        355                 360                 365

Leu Thr Phe Gly Leu Tyr Leu Ser Ile Lys Leu His
370                 375                 380

<210> SEQ ID NO 3
<211> LENGTH: 9377
<212> TYPE: DNA
<213> ORGANISM: Human

<400> SEQUENCE: 3
ccagtatggt ctcaatctcc tgtccttgtg atctgcctgt cttggccttc caaagtgctg      60
ggattacagg tgtgagccac cgtgcccgac ctttttttt ttttaaagac aggatctcac     120
tctgtcaacc aggctggagt gcagtgccat gatcatagct cactgcaata ccaccacgcc     180

-continued

```
cagctaattt taaaattttt tgtggagtgg gtgggggggg tctccctatg ttgctcaggc     240
tggtcttgag ctcctgggct caagtgatcc tcccgcctca gtctcccaaa gcactaggat     300
tgcaggtgtg agccaccatg cctggctgtg gctgacccct tgtatgccta aatcaggcag     360
tcattggcta cccctgtcag tgggggtgaa acctccaggt ggtttctagg ctagctgact     420
cctgccagcc aagcacaatt ctccagagaa cacaggcata taagccttgt ccaccagcga     480
agcagcagct ggggccgggc acattggtgg tgaaggcctt ctgggtgaga catcaacagt     540
gtttgcaaca atcatttaaa gagttattta acatcaggct gggtgtggtg gctcatgcct     600
gtaatcctaa cactttggga ggctgaggta ggcagatcac ttgaggtcag gagtttgaga     660
ccagtctggc caacgtggtg aaaccctgtc tctactaaaa atacaaaaaa aagccgggcg     720
cagtgactca cgcctgtaat cccagcactt tgggaggccc aggtgggcag atcacctgag     780
gtctggagtt tgagaccagc ctgatcaaca tggagaaatc cccctctcta ctaaaaatac     840
aaaattagtt gggtgtggtg gcgcatgcct gtaatcccag ctactcggga ggctgaggca     900
ggagaatctc ttgaacctgg gaagcagagg ttgcagtgag ccgagatcac accactgcac     960
tcccaagtgg gcagcaagag cgagactctg tctcaaaaaa aaaagagaga gtcattaaac     1020
atcaaaagga aaagaaagca agcaatatgc agactgactc tatagaggct ggctcttttc     1080
tccccttggc ctctgctgtc tatacttact agttggctgt cattgaaact taacaaatgg     1140
ccaggtgtgg tggctcatgc ctgtaatccc agcagtttgg gaggccaagg caggcagatc     1200
acctgaggca aggagttcga gactatcgac aaagtgagac tccatctcaa aaaaaaaaa     1260 aaccaaaaaa agaaagaaaa agaaacttaa caaacatatg tagaagtctt ggctctagat     1320
aactgagaga aataggactg gcttagtgag ttgccaatta tattctaata ataggattct     1380
ttattaaaac aactgtggaa gaaacagtg tttgcttttt attccttttg aaatctgggg     1440
cactttgcaa aatggaaatc aatgcctcga cttgcattgg tgtgtgatct ggggttttg     1500 cttctgcagg agaagcccta tctggcttat tggctgcctg ccttgcccta tgtctttctt     1560 tcttttttt tttttttaatt tgtataaatg tgtgaagtac aagtgtaatt tgttagatg     1620 catacatcgc atagtggtga agtcagggct tttagggtat ccataacccc aacaatgtac     1680
attgtatctg ttaagtaatc tcccattatc cttgccctgt catctaagga gtgggcttgt     1740
tactttggac tgagccacct ggggctagag aagagaaggc attgagtgag ggaaacgggc     1800
ttgggaattc cggagattgt tatcctgccc tgccgctgt ctgaggggat tctcctcaag     1860
taccctggaa tgttcctgtg gcccctgtgg atcgccacca caaagatcat gaggttctgt     1920
tgccctggca acccgttgtc cagcgcctct gcactgggc tgccaaggtt ccaggaagag     1980
gcaggactgc ccggcccagc cttggaggaa gacttctggg cagaagcgga acacaggagc     2040
agagacacat agtcttggct ccagtttcgt ttcagttatg cccacccttt cagtgttcat     2100
ggatgtgccc ctcgcccaca agctagaggg cagcttgtta aagacctaca aacaagatga     2160
ttacccgaac aagatattct tagcctatag aggtagatgc ctagcagttc tgaagtataa     2220
gacttaagtg atggtaactg cctctaggag gacagtgttc cctgctgcag ggggaggggt     2280
gcagcccaag cttctgtggg tggagagatc ttttcttgtt aacagaatta cccagtgggg     2340
aaaagtgcag ataaggtccc aggtcattcc atgctctctg cccttctctg ggggcttcta     2400
gggatttggt gagagctatg tcctcttcca caactctatg cttggggcc tgcatggcca     2460 tcccacactt cttcagattc ttacctcctc tctctctctt tctctttctc ttcctgttct     2520
tgaaccaaga atggttctcc agattgagcc ttctgctatg caactggggc tcaccactgt     2580
```

```
gaaagtcagg gttacctttta tttagcttca tctacctata actctcattt tgcatatata    2640
tatatatata tatatatata tatatatata tatatatata tttttttttt ttttcttgag    2700
acagggcctc actctgttgc ccaggctgaa gtgcagtggc aaggatctca gctcactgcc    2760
acctttgcct cctgggctca aaccatcctc ttgcctcagc ctcctgagta gctgggacta    2820
caggcgctgg tcaccatgtc tggctgtttt gtattttttt gtagagacag ggtttcatca    2880
tgttgcccag gctgatcttg aactcctgaa ctcaagtgat ccacccacct tagcctcccg    2940
aagtgctggg attacaggcc tgagccacca atcctgggct tgtatgattt ttaacctttta   3000 aaatggcata ggtttcagtt gtctttttta aaaagacaaa aataatacac attcactaac    3060
agcatattct tttcatcaag gagaaaagaa aagggaaagt tgtatttttca caggcacctt    3120 cccacagccc catggagtcc aggagagatt tgtttgcagg ctgtctgcag agctcagccc    3180
tgggggccca aaccaggcat ctggagctcc ctctgtggtt ttcctcacag tctgcatgac    3240
aaatgaaggc catccctggg tttctctcgt ggtgcagaag actcgactac agatttcaca    3300
ggatccctcc ctgaattatg agtacttgcc caccatgggc ctgaaatcat tcatccaggc    3360
ctctctagca ctcctctttg gaaagcacag ccaagccatt gtggagaaca gggtgagaag    3420
gtgggccctc ccctggctca tttagacaca gagagtggcg atctgggtct gcacaacctt    3480
aaacccgaag gggacctcgg agggccccct ggtattgata aagagatac ctgaggctca     3540 gagagtccac aagtccttag ccatcgagtc aggatcggaa tctcagtcca gtggtattcc    3600
cacctgctca cactgctgat tgaaagctc tttcaagaca ggaatgatct gaattggagg     3660
tggtgttagt attcccatta ctgttttatt ttttaaccta ttatatatat tttttgagac    3720
agagtctcac tctgtcaccc aggctagagt gcagtggtgc catctcagct cactgcaacc    3780
tccacctccc aggttcaagc aattctggtg ctgcatcctc ctgagtagct ggaatcacag    3840
gcatgtgcca tcacgcccag ctaattttttg tattttttgt agagacaggg tttcaccatg    3900
ttggccaggc tggtctcaaa ctcctggcct caggggattc cctgcctcgt cctcccaaag    3960
tgctgggatt acaggcatga gctactgcgt ctcgcctcca ttactgtttt agagtgttat    4020
ttctgtctat ttcttttttat ttttttaatgt ttatttactt attatttttt tgagacggag   4080
tctcactctg tcacccagac tggagtgcag tggcctgatc tccgctcact gcaacttccg    4140
ccttccgggt tcaagtgatt ctcctgcctc agcctcttga gtagcgggga ttacaggtgc    4200
ccaacaccac atccggctaa ttttttgtatt tttagtagat acggggtttc aacatgttgg    4260
ccatgacctc gagtgatcca ccccccccgg cctcccaaag tgctggaatt acaggtgtga    4320
gccaccacac ctggcctatt tgtgtctatg tcttgctgga aggtagggggg tgtacacact    4380 gttggtgaca gtggtgcctt ccagcttggc gtccagtttc tcagagcttg cataaggat     4440 gctcgtatag tttacatcat ctcttctcaa aaaggttagt cttacccaag atgagtggaa    4500
cagcaatccc cgtcccttgt tcctaatcct cacccctttt gccatcttca ctgttatccc    4560
tcattctctg tcatgagcaa aatggcagac aagccaagct atttatgtcc ttttcctgtt   4620
aatgtcccac cttcagccag tgactctcag ccccacactc cagtacctct gtctccgtct    4680
ctctgtttcc catgtaccag ctagtggggg gctgtgttcc cacagaactg catggactcg    4740
tcttccagga catgggcttt acagtttatg aatactctgt ctgggacccc aagaagctat    4800
gcatggaccc cgacatactc ctcaatgtgg tggaggtaga gggccccgc tcagaaactc     4860 ctccctagag ctgacttaca gcctaatgtt cctctcctcc ccacacctct taagtcatcc    4920
```

```
aagacctttt ccaggtttga atttgcctgg cccttcaatg gtaactaaca tggaggagca    4980
cttcaccccc aaatgccctg gggccgccac tcctgggtgg gggtgaagcc tgatgagacc    5040
gtctgtacct gcagcagatc ccacatggct gtgtccttgt gatggggaac attatcgact    5100
gcaagttgac accaagtggg tgggcaaagt tgatgtccat gataaaggta aacccaatct    5160
cccacccgac cttcctgtct ttgactctct gctctctcct ccatctgtct cattctttt    5220
ttgttctcct ttctcctaca gagcaagcag atattcccat tttttgatat tccctgtcaa    5280
ggtttataca ccagtgactt ggaagaagat actagaatct tacaatactt tgtgtctcaa    5340
ggctttgagt tcttctgcag ccagtctctg tccaagaatt ttggcattta tggtatggta    5400
caggcagaag aagggagggt ctgttgctga agtggtgctg cgctcacagc acagtgatgt    5460
ttttgatatc tcatccttgg gagggagcca aggactctag ggagagcact atagaagcag    5520
aagtggggag cactgagcta gaatttggtt ctgttactaa atctagtaac agaacccaac    5580
ccagcttggc ttggatcatt tcaccccctc aggcctctgt ttcctcaact ataagatgag    5640
agggtggggc tggcatggtg ggtgacacct gtaatcccag ttgacacctc ctaatccctc    5700
ctttgggagg tcaaggttag gtgatcactt gaggccagga attcaagacc agcctgggca    5760
acacaccgag acccggtctc tacaaacaat taaaaaaatt agtcgggcat ggtggtacac    5820
accagtagtc ctacccaccc gggggctga ggcaggagga ttgcttaagc ccaggaggta    5880
gaggttgcag tgagctatga ttccaccatt gcactctagc ctgggcaaca gagagagatg    5940
gtcactttaa acaaataaaa ataaaaataa aataaaaaa ggaaaggaaa ggaaaaaaca    6000
ggagagtaga acttagtgat ctttcaaatt ccttcctcct ttaagactct gacttatggg    6060
tacttttgct ggaaggagag cctctggcaa cttcccggag cctgaatatc accctggctg    6120
ggctgcaatg agggccttgt ggttcaaccc tttcttctgc aaggttgggg gttgagatct    6180
aggtgaaggc cttgggagtg gaggaagggg ctgaggctga ggctgtcttc ccaacactgc    6240
agatgaagga gtggggatgc tagtggtggt ggcagtcaac aaccagcagc tgctgtgtgt    6300
cctctcccag ctgaaggat tagcccaggc cctgtggcta aaccccccca acacgggtgc    6360
acgtgtcatc acctccatcc tctgcaaccc tgctctgctg ggagaatggt aagggtgagg    6420
gctggagcag gaagggatgg gagaggccct gggtgcctgc agacctgctg atctgcagga    6480
tcggcaggg tgcttctctc ctgcccatgt ggccttttta ctccattcat tcatcaacat    6540
ttactaagga cctgatgtgt accaatggcg gtggctatgc caagggttgc cttaggggac    6600
agagtgatag gacatttgtt ttgcacccag gccaatgagt tatatgaact cttccagatt    6660
gcttgggag ataagagagc atcagggct tgcaactctg gcaaaatctg cctgggagcc    6720
tccctggttt gcttaaatga atatgagatc aaacctccct cccactcata atcatcccag    6780
agcctctggc actctgttgg agacctttga aggtaagaag agtggactgg caatgaggga    6840
ggtttgaggg caaggggac ctcacaccct cctttctcat tgtccttcct tggtaggaag    6900
cagagtctaa aagaagttgt agagaacatc atgctaacca aggaaaaagt gaaggagaaa    6960
ctccagctcc tgggaacccc tgggtcctgg ggtcacatca ccgagcagag tgggacccac    7020
ggctatcttg gactcaactg taagggtcta ggggctggt gtcccccctt tctgaccttt    7080
ggcctgtatt tgagcattaa acttcactga ctaggtgacc agttcctagc ttcactccag    7140
attttgattc tgtcctctgg aaaatggct gctttaaaga cacttctgga cccccagaag    7200
taccgacact cccatatcctt cataaaccag cctgggtgcc cggtgcagtg gctcatgcct    7260
gtaatcccaa cactttgaga ggccgaggcg ggtgggtcac ctgaggtcag gagttcgaga    7320
```

```
ccagcctggc caacatggtg aaaccccgtc tctactaaaa aataaaatat gaaaattagc      7380
cgtgcatggt ggtgcatcct gtaatcatag ctacttggga ggttgaggca ggagaatcgc      7440
ttgaacctgg gaggcgaagg ttgcagtgag ccaagattgc accattgaac tccagcctgg      7500
gcaacaagag caaaactcca tctcaatcaa tcaatcaata aaaaaataag aaaataaacc      7560
agcctgggct agaggagaat tcgagatggc cagtctcgag atctgagacc ttgtcatgat      7620
tttagcccag caggtggaat acctggtcag gaagaagcac atctatatcc ccaagaacgg      7680
tcagattaac ttcagctgta tcaatgccaa caacataaat tacatcactg agggcatcaa      7740
tgaggctgtc ctcctcacag agagctcaga gatgtgtctt ccaaaggaaa aaaaaacact      7800
gattggaata aaactttagt ctttgcaaaa atcttgtgct gattattcat tactacaatt      7860
catttctttg cttatttatg aagcagtggt ctggcctcag tacagagaaa gagacagaga      7920
gaaagagaga gagaaaggcc cagagggaa gggtgtatct accttcattg gccatctcat      7980
atttattgag cacctactac attaaggccc tgagctggcc gtgaaaggga gtacaaaaaa      8040
caggtagaaa ccagcctgtt ttctccagac acttacagtc tagttgggag acaagcctta      8100
gtcacataaa acacttaagt aacattttaa ggctgaatgt gacagaagtc agaatatata      8160
aacagaaaat gtgccaggaa tttagaaaag aaatacgtca aagtgggcca gaatagatgg      8220
ggagcatctc atgaggaggt agcacttgat tgggatattg atagacagat gaatggattg      8280
gatgaataat aactaataga agctggaagg atatcctagg tcaataacaa cctgagcaag      8340
tgtcactgac atgataagaa aaaataaatg tttatcgggc agctactaat acatgggact      8400
ctgcaaactc ccaggatacc aacaggtata tgacacagtt ggtgccctcc actctcgttg      8460
gggagacaca atttatatgg ttgaaaggaa aaactctttt ttctctctcc tctactgtga      8520
ttctcaattc tgacaccaga ttgtataggg ttttcccac acaattaatt ccgttctttg       8580
gtagacatca gttgggtgtc ttaaaattca atagattctt ttttattttt tcttttcttg      8640
ggatggcgtc tctgtcgccc aggctgcagt gcagttgtgc aatctcagct cactgcaact      8700
gccacctccc aggttcaaga gattctcttg cctcagtctc ccaagtagct gggactacag      8760
gtatgtgcca ccacgcccgg ctaattttg tattttgtt agagacgggg tttcgccatg       8820
ttggccaggt tggtcttgga ctcctcttct caggtgatcc acccgcctca gcctctgaaa      8880
atgccgggat tacaggcgtg aaccaccatg cccagcccaa ttcaatagat tctgatacta      8940
cctacctgga gttagcatca aattccagag gtgaatggct cagttctgca agactgcacc      9000
ccgtgaatgg ctcagttctg caagactgca ccccacttca gatgccagtc acatgtccag      9060
tggtgtgact tgtgcatctg ctataaactg gggttcctac cactccttcc ttgggtttga      9120
taatttgcca gaacaattca catatctcag gaaaatagtt tatttactag attatcagtt      9180
tgttataaaa ggatgcaact caggaacagc cagatggaag acacgcatag ggaaaggggc      9240
gtggagcttc catggtctct ctgggttcgc cctcccagct cctccatatg ttcagcaacc      9300
tggaagctct cccaaaccct ttagttaggg gttttttatga aggcttcatt gcacaggcat      9360
gatggactaa aacattg                                                    9377
```

<210> SEQ ID NO 4
<211> LENGTH: 254
<212> TYPE: PRT
<213> ORGANISM: Mus musculus

<400> SEQUENCE: 4

-continued

```
Met Thr Ser Leu Ser Val Phe Arg Asp Val Pro Thr Ala Gln Lys Leu
  1               5                  10                  15

Glu Gly Ser Leu Leu Lys Ile Tyr Arg Gln Asp Gly Tyr Pro Ser Lys
             20                  25                  30

Leu Phe Leu Ala Tyr Lys Val Cys Met Thr Glu Glu Gly His Pro Trp
         35                  40                  45

Val Ser Leu Val Val His Lys Thr Arg Leu Gln Ile Ala Glu Asp Pro
 50                  55                  60

Ser Leu Asp Tyr Glu Tyr Leu Pro Leu Val Gly Leu Lys Ser Phe Ile
 65                  70                  75                  80

Gln Ser Ser Leu Glu Leu Leu Phe Gly Lys His Ser Glu Ala Ile Ala
                 85                  90                  95

Glu Lys Arg Val Gly Val His Ile Val Gly Glu Ser Gly Ala Phe
            100                 105                 110

Gln Leu Gly Ala Gln Phe Leu Lys Thr Trp Arg Lys Asn Val Lys Ile
            115                 120                 125

Val Cys Ile Val Ser Cys Gln Lys Glu Gln Cys Gly Leu Ile Phe Gln
130                 135                 140

Asp Met Gly Phe Ile Val Tyr Glu Tyr Ser Ile Trp Asn Ala Ser Asp
145                 150                 155                 160

Leu Cys Ser Asp Pro Ser Met Phe Val Glu Val Leu Gln His Ile Pro
                165                 170                 175

Val Gly Ser Ile Leu Val Ile Gly Asn Ile Thr Asp Cys Lys Phe Thr
            180                 185                 190

Gln Asn Gln Trp Thr Lys Leu Met Ser Ile Ile Lys Ser Lys Gln Ile
            195                 200                 205

Phe Pro Phe Asp Ile Pro Cys Gln Gly Leu Ser Thr Gly Asp Leu
    210                 215                 220

Glu Glu Asp Thr Lys Ile Leu Gly Tyr Phe Val Ser Leu Gly Leu Glu
225                 230                 235                 240

Phe Phe Cys Ser Gln Ser Leu Ser Lys Asn Phe Gly Ile Tyr
                245                 250
```

<210> SEQ ID NO 5
<211> LENGTH: 365
<212> TYPE: PRT
<213> ORGANISM: Human

<400> SEQUENCE: 5

```
Ser Val Phe Ala Glu Val Pro Gln Ala Gln Pro Val Leu Val Phe Lys
  1               5                  10                  15

Leu Thr Ala Asp Phe Arg Glu Asp Pro Asp Pro Arg Lys Val Asn Leu
             20                  25                  30

Gly Val Gly Ala Tyr Arg Thr Asp Asp Cys His Pro Trp Val Leu Pro
         35                  40                  45

Val Val Lys Lys Val Glu Gln Lys Ile Ala Asn Asp Asn Ser Leu Asn
 50                  55                  60

His Glu Tyr Leu Pro Ile Leu Gly Leu Ala Glu Phe Arg Ser Cys Ala
 65                  70                  75                  80

Ser Arg Leu Ala Leu Gly Asp Asp Ser Pro Ala Leu Lys Glu Lys Arg
                 85                  90                  95

Val Gly Gly Val Gln Ser Leu Gly Gly Thr Gly Ala Leu Arg Ile Gly
            100                 105                 110

Ala Asp Phe Leu Ala Arg Trp Tyr Asn Gly Thr Asn Asn Lys Asn Thr
            115                 120                 125
```

```
Pro Val Tyr Val Ser Ser Pro Thr Trp Glu Asn His Asn Ala Val Phe
        130                 135                 140

Ser Ala Ala Gly Phe Lys Asp Ile Arg Ser Tyr Arg Tyr Trp Asp Ala
145                 150                 155                 160

Glu Lys Arg Gly Leu Asp Leu Gln Gly Phe Leu Asn Asp Leu Glu Asn
                165                 170                 175

Ala Pro Glu Phe Ser Ile Val Val Leu His Ala Cys Ala His Asn Pro
            180                 185                 190

Thr Gly Ile Asp Pro Thr Pro Glu Gln Trp Lys Gln Ile Ala Ser Val
        195                 200                 205

Met Lys Arg Arg Phe Leu Phe Pro Phe Phe Asp Ser Ala Tyr Gln Gly
        210                 215                 220

Phe Ala Ser Gly Asn Leu Glu Arg Asp Ala Trp Ala Ile Arg Tyr Phe
225                 230                 235                 240

Val Ser Glu Gly Phe Glu Phe Phe Cys Ala Gln Ser Phe Ser Lys Asn
                245                 250                 255

Phe Gly Leu Tyr Asn Glu Arg Val Gly Asn Leu Thr Val Val Gly Lys
            260                 265                 270

Glu Pro Glu Ser Ile Leu Gln Val Leu Ser Gln Met Glu Lys Ile Val
        275                 280                 285

Arg Ile Thr Trp Ser Asn Pro Pro Ala Gln Gly Ala Arg Ile Val Ala
        290                 295                 300

Ser Thr Leu Ser Asn Pro Glu Leu Phe Glu Glu Trp Thr Gly Asn Val
305                 310                 315                 320

Lys Thr Met Ala Asp Arg Ile Leu Thr Met Arg Ser Glu Leu Arg Ala
                325                 330                 335

Arg Leu Glu Ala Leu Lys Thr Pro Gly Thr Trp Asn His Ile Thr Asp
            340                 345                 350

Gln Ile Gly Met Phe Ser Phe Thr Gly Leu Asn Pro Lys
        355                 360                 365
```